United States Patent
Ocaranza Jeraldino et al.

(10) Patent No.: US 9,511,120 B2
(45) Date of Patent: Dec. 6, 2016

(54) USE OF THE ANGIOTENSIN-(1-9) PEPTIDE OR DERIVATIVES THEREOF, USE OF VECTORS OVEREXPRESSING THE ACE2 ENZYME THAT PRODUCES ANGIOTENSIN-(1-9) FOR PREPARING MEDICAMENTS USEFUL FOR PREVENTING, REVERTING, INHIBITING AND/OR REDUCING HYPERTENSION AND/OR INDUCING VASODILATION

(75) Inventors: Maria Paz Ocaranza Jeraldino, Santiago (CL); Jorge Emilio Jalil Milad, Santiago (CL); Sergio Alejandro Lavandero González, Santiago (CL); Mario Martin Chiong Lay, Santiago (CL); Luis Fernando Michea Acevedo, Santiago (CL)

(73) Assignees: PONTIFICA UNIVERSIDAD CATÓLICA DE CHILE, Santiago (CL); UNIVERSIDAD DE CHILE, Piso (CL)

(*) Notice: Subject to any disclaimer, the term of this patent is extended or adjusted under 35 U.S.C. 154(b) by 0 days.

(21) Appl. No.: 14/390,663

(22) PCT Filed: Apr. 5, 2012

(86) PCT No.: PCT/CL2012/000016
§ 371 (c)(1),
(2), (4) Date: Dec. 10, 2014

(87) PCT Pub. No.: WO2013/149355
PCT Pub. Date: Oct. 10, 2013

(65) Prior Publication Data
US 2015/0190472 A1    Jul. 9, 2015

(51) Int. Cl.
| | |
|---|---|
| *A61K 38/22* | (2006.01) |
| *A61K 38/08* | (2006.01) |
| *A61K 38/48* | (2006.01) |
| *A61K 38/55* | (2006.01) |
| *A61K 45/06* | (2006.01) |

(52) U.S. Cl.
CPC .............. *A61K 38/22* (2013.01); *A61K 38/085* (2013.01); *A61K 38/4813* (2013.01); *A61K 38/553* (2013.01); *A61K 38/556* (2013.01); *A61K 45/06* (2013.01)

(58) Field of Classification Search
None
See application file for complete search history.

(56) References Cited

U.S. PATENT DOCUMENTS 7,468,390 B2 * 12/2008 Ksander et al. .............. 514/533

OTHER PUBLICATIONS

Ocaranza, M.P., et al "Protective Role of the ACE2/Ang-(1-9) Axis in Cardiovascular Remodeling," Int J Hypertens. 2012; pp. 1-12.*
C. D'iez-Freire, J. V'azquez, M. F. Correa De Adjounian et al., "ACE2 gene transfer attenuates hypertension-linked pathophysiological changes in the SHR," Physiological Genomics, vol. 27, No. 1, pp. 12-19, 2006.*
Treatment definition of treatment by The Free Dictionary 2016 pp. 1-5.*
Diovan (Valsartan) Drug Information: Description, User Reviews, Drug Side Effects, Interactions Prescribing Information at RxList 2016 pp. 1-3.*
Chen, Zhenlong; et al., "Hydrolysis of Angiotensin Peptides by Human I-Converting Enzyme and the Resensitization of B2 Kinin Receptors," Hypertension (2005), 46(6), 1368-1373.*

* cited by examiner

*Primary Examiner* — Thomas S Heard
(74) *Attorney, Agent, or Firm* — Birch, Stewart, Kolasch & Birch, LLP

(57) ABSTRACT

The present invention is related to the use of the angiotensin-(1-9) peptide or peptides derived therefrom, which are biological or chemical analogs, for preparing medicaments useful for preventing, reverting, inhibiting and/or reducing hypertension and/or inducing vasodilation. Furthermore, this invention also comprises a vector overexpressing the homologous angiotensin-II converting enzyme (ACE2) for elevating the concentration in the blood and/or tissues of the angiotensin-(1-9) peptide. This vector may be adenovirus, retrovirus, lentivirus or adeno-associated virus containing the gene encoding for ACE2. This invention allows the administration of angiotensin-(1-9) or the derivatives thereof in oral form, injectable form, continuous infusion pump, or for increasing its levels in the body by means of the combined treatment with angiotensin-I converting enzyme inhibitors, with angiotensin-II receptor antagonists (ARA II), with Rho kinase inhibitors, with renin inhibitors, with L-type calcium channel antagonists and/or with diuretics.

24 Claims, 23 Drawing Sheets
(5 of 23 Drawing Sheet(s) Filed in Color)

A

B

A

Cardiomyocyte Area

B

Cardiomyocyte Perimeter

A

B

USE OF THE ANGIOTENSIN-(1-9) PEPTIDE OR DERIVATIVES THEREOF, USE OF VECTORS OVEREXPRESSING THE ACE2 ENZYME THAT PRODUCES ANGIOTENSIN-(1-9) FOR PREPARING MEDICAMENTS USEFUL FOR PREVENTING, REVERTING, INHIBITING AND/OR REDUCING HYPERTENSION AND/OR INDUCING VASODILATION

The present invention is related to the field of the renin-angiotensin-aldosterone system, and in particular to the peptide angiotensin-(1-9) or derivatives thereof, which are chemical or biological equivalents. In particular, the present invention relates to the use of the peptide angiotensin-(1-9) and/or derivatives thereof and anti-hypertensive effects, specifically for preventing, reversing, inhibiting and/or reducing blood pressure and/or for inducing vasodilation. Further, this invention includes the field of increasing the concentration of the peptide angiotensin-(1-9) in the blood and/or tissues via the increased endogenous production of angiotensin-(1-9) through a vector expressing ECA2, which is the enzyme responsible for endogenously producing angiotensin-(1-9).

Hypertension (HTN) is a risk factor for developing cardiovascular diseases (CVD). The latest National Health Survey (NHS) conducted in 2003 showed that HTN has a prevalence of 33.7% in the general population. According to the World Health Organization (WHO), increased blood pressure is considered as one of the major cardiovascular risk factors for CVD, since a chronic increase ends up damaging target organs, such as the heart, arteries, kidney and brain (Varagic & Frohlich, J. Mol. Cell Cardiol. 34:1435-42, 2002).

Increased activation of the renin-angiotensin-aldosterone system (RAAS), specifically, the classic route with more activity of the angiotensin-I-converting enzyme (ACE) and higher levels of angiotensin II have been identified as major determiners of the etiology of hypertension (HTN), heart failure, in pathophysiological processes of cardiovascular remodeling, diastolic dysfunction and impaired vasodilation of resistance arteries. Both ACE and angiotensin II represent the main therapeutic targets of the current treatment of HTN (Varagic & Frohlich, J. Mol. Cell. Cardiol. 34:1435-42, 2002).

The RAAS cascade is initiated by the action of renin on the circulating hepatic angiotensinogen. This reaction produces angiotensin I, which is physiologically inactive. Angiotensin I is converted into the biologically active octapeptide angiotensin II through the action of ACE (Okunishi et al., Jpn J. Pharmacol. 62:207-10, 1993). ACE is a zinc-dependent metallopeptidase, mainly found in lungs, but also in the heart, blood vessels, kidney as well as plasma (Campbell, J. Cardiovasc. Pharmacol. 10:S1-S8, 1987; Johnston et al. J. Hypertens. Suppl. 10:S13-26, 1992). In human beings, tissue angiotensin II is also produced by other enzymes, such as chymase and tissue plasminogen activating factor (Reilly et al., J. Biol. Chem. 257:8619-22, 1982; Gibbons & Dzau, N. Engl. J. Med. 19:1431-8, 1994). ACE is also responsible for the catabolism and inactivation of vasodilators such as bradykinins (BKs) (Tschöpe at al. J. Cardiovasc. Pharmacol. 39:478-87, 2002).

RAAS is involved in the development of HTN (Dzau, J. Hypertens. Suppl. 6:7-12, 1988; Bader at al., Exp. Physiol. 85:713-731, 2000; Bader et al., J. Mol. Med. 79:76-102, 2001), with regard of insulin resistance (Henriksen & Jacob, Diabetes Obes. Metab. 5:214-22, 2003; Yavuz et al., J. Renin Angiotensin Aldosterone Syst. 4:197-203, 2003), metabolism of nitric oxide (Liu and Person, Hypertension 43:649-53, 2004), oxidative stress (Zhou et al., Am. J. Hypertension 17:167-71, 2004), and both cardiac and vascular smooth muscle hypertrophy (Higashi et al., Circ. Res. 93:767-75, 2003; Yamakawa et al., Eur. J. Pharmacol. 478:39-46, 2003).

Angiotensin II acts on target cells via G protein-coupled receptors, subtypes 1 and 2 (ATR1 and ATR2, respectively) (Berry et al. Am. J. Physiol. 281:H2337-H2365, 2001; de Gasparo, Drugs 62:1-10, 2002). The activation of ATR1 causes most of the cardiovascular actions of angiotensin II, such as vasoconstriction, mitogenic and hypertrophic effects, inflammatory response, and water and salt retention (de Gasparo et al., J. Renin Angiotensin Aldosterone Syst. 1:151-8, 2000). These effects are mediated by a complex interaction of intracellular signaling pathways involving several phospholipases (PLC, PLD, PLA2), stimulation of NAD(P)H oxidase and reactive oxygen species ($O_2^-$, $H_2O_2$), activation of gene transcription (proto-oncogenes: c-fos, c-jun, c-myc), and tyrosine kinase activation (Src, JAK/STAT, FAK, Pyk2, p130Cas and PI3-kinase). Some of these actions can be mediated, either directly or indirectly, by transactivation of tyrosine kinase receptors (Touyz & Berry, Braz. J. Med. Biol. Res. 35:1001-15, 2002). Unlike ATR1-mediated actions, ATR2 triggers apoptosis, BK-mediated vasodilation and natriuresis, and nitric oxide (NO) (de Gasparo et al., J. Renin Angiotensin Aldosterone Syst. 1:151-8, 2000).

Recently, a pathway parallel to ARS initiated by the homologous angiotensin-I-converting enzyme (ACE-2) (Donoghue et al., Circ. Res. 87:e1-9, 2000; Tipnis et al., J. Biol. Chem. 275: 33238-43, 2000) has been discovered. Originally, this enzyme was found in testicles, kidneys and heart, but real-time PCR studies conducted later showed that it is also expressed in the gastrointestinal tract, brain, lungs, aorta, and liver (Harmer at al., FEBS Lett. 532:107-10, 2002; Ferrario, Hypertension 47:515-21, 2006). At cellular level, ACE2 has been mainly found in the epithelium of the renal tubule, macrophages, cardiomyocytes, endothelium of small and large arteries and smooth muscle of these vessels (Burell et al., Eur. Heart J. 26:369-75, 2005). ACE2 exhibits 40% homology in its catalytic domain to ACE, and it is an ectoenzyme, whose catalytic sites are oriented towards the extracellular space and, therefore, it hydrolyzes extracellular peptides. Furthermore, the same as ACE, ACE2 is capable of detaching from the cell surface, and it exhibits a topology of a type I integral membrane protein. Despite this similarity, ACE-2 differs from ACE in its substrate specificity and in the lack of inhibition by conventional ACE inhibitors.

In RAAS, ACE2 competes with ACE for hydrolysis of the inactive decapeptide angiotensin I to form angiotensin-(1-9) (Donoghue et al., J. Mol. Cell Cardiol. 35:1043-53, 2003); therefore, the amount of angiotensin I available for the generation of angiotensin II by the action of ACE decreases. Although the effects of angiotensin-(1-9) on the heart and kidney have not been described (Danilczyk & Penninger, Circ. Res. 98:463-71, 2006), there are several studies showing that angiotensin-(1-9) promotes the angiotensin-II-mediated vasoconstriction in rat aortic rings and has vasopressor effects in conscious rats (Huang et al., J. Biol. Chem. 278:15532-40, 2003). Furthermore, it has been found in human and rat plasma that angiotensin-(1-9) levels are higher than those of angiotensin II (Johnson, Peptides 10: 489-92, 1989) and that this peptide accumulates in animals treated with ACE inhibitors (Drummer, Biochem. Pharmacol. 39:513-8, 1990). Other studies report that angiotensin-(1-9) promotes the binding of bradykinin to its B2 receptor probably due to conformational changes in the ACE-B2 receptor complex (Erdos et al., J. Mol. Cell. Cardiol. 34:1569-76, 2002).

ACE2 has higher catalytic efficiency (400 times) to hydrolyze angiotensin II than angiotensin I and to form the vasodilator peptide angiotensin-(1-7) (Donoghue et al., Circ. Res. 87:e1-9, 2000; Vickers et al., J. Biol. Chem. 277:14838-43, 2003; Rice et al., Biochem. J. 383:45-51, 2004). The latter is also generated by the hydrolysis of angiotensin I through the action of neutral endopeptidase (NEP), prolyl endopeptidases or ACE (Welches et al., Life Sci. 52:1461-1480, 1993; Vickers et al., J. Biol. Chem. 277:14838-43, 2003). Thus, ACE2 plays a central role in the balance of the vasoconstrictor and proliferative activity of angiotensin II via its ATR1, increasing levels of angiotensin-(1-7) (Der Sarkissian et al., Prog. Biophys. Mol. Biol. 91:163-98, 2005).

However, there is no evidence to indicate whether angiotensin-(1-9) and/or derivatives thereof act preventing, reversing, inhibiting and/or reducing hypertension and/or inducing vasodilation.

```
Angiotensinogen* (SEQ ID NO: 1):
Asp-Arg-Val-Tyr-Ile-His-Pro-Phe-His-Leu-Leu-Val-
Tyr-Ser Angiotensin I (SEQ ID NO: 2):
Asp-Arg-Val-Tyr-Ile-His-Pro-Phe-His-Leu Angiotensin II (SEQ ID NO: 3):
Asp-Arg-Val-Tyr-Ile-His-Pro-Phe Angiotensin III (SEQ ID NO: 4):
Arg-Val-Tyr-Ile-His-Pro-Phe Angiotensin-IV (SEQ ID NO: 5):
Val-Tyr-Ile-His-Pro-Phe Angiotensin-(1-9) (SEQ ID NO: 6):
Asp-Arg-Val-Tyr-Ile-His-Pro-Phe-His Angiotensin-(1-7) (SEQ ID NO: 7):
Asp-Arg-Val-Tyr-Ile-His-Pro
```

The first amino acid of the sequences corresponds to the amino terminus. R: remaining sequence of angiotensinogen.

Several physiological and biological functions for various angiotensins have been described.

Des-aspartate-angiotensin I has been described to be used in the treatment and/or prevention of cardiac hypertrophy (U.S. Pat. No. 5,773,415) and formation of neointima or restenosis (U.S. Pat. No. 6,100,237).

Angiotensin II is involved in the control of blood volume, blood pressure, cardiac hypertrophy and neointimal formation. Activation of ATR1 by angiotensin II favors cardiac hypertrophy (Dostal & Baker, Am. J. Hypertens. 5:276-280, 1991), neointimal formation (Osterrieder et al., Hypertension 18:1160-4, 1991; Daemen et al., Circ. Res. 68:450-6, 1991), boosts vasoconstriction, sodium retention and production of reactive oxygen species (ROS) (Berry et al., Am. J. Physiol. 281:H2337-H2365, 2001).

Angiotensin III mediates AT2 receptor-dependent natriuresis induction. It induces vasoconstriction and aldosterone release (Fyhrquist & Saijonmaa, J. Intern. Med. 264:224-36, 2008).

Angiotensin IV, a metabolite secondary to angiotensin II, has antihypertrophic actions and also inhibits neointimal formation (EP1846017).

Angiotensin-(1-7) is involved in actions which oppose the actions of angiotensin II. It has been described as a vasodilation-inducing peptide, with antihypertensive and antifibrotic effects (Katovich et al., Curr. Hypertens. Rep. 10:227-32, 2008).

Results from our laboratory in an experimental model of late remodeling after myocardial infarction (MI) showed higher enzymatic activity of ACE and angiotensin II levels, and decreased enzyme activity of ACE-2 and levels of angiotensin-(1-9) (Ocaranza et al., Hypertension 48:572-8, 2006). These changes favored myocardial fibrosis and pathological ventricular hypertrophy (Ocaranza et al., Rev. Chil. Cardiol. 26:63-76, 2007). The inhibition of ACE with enalapril or the blocking of the angiotensin II type 1 receptor (ATR1) prevented the decrease in ACE-2 activity and significantly increased levels of angiotensin-(1-9) (Ocaranza et al., Hypertension 48:572-8, 2006; Ocaranza et al., Rev. Chil. Cardiol. 26:63-76, 2007). These results suggested an interaction between ACE and ACE-2 in myocardial remodeling after MI, and also that angiotensin-(1-9) rather than angiotensin-(1-7) would act as a counter-regulator of angiotensin II (Ocaranza et al., Hypertension 48: 572-8, 2006).

Recently, we filed the Chilean patent application CL3736-2008 and the international patent application PCT/CL2009000029, related to a pharmaceutical composition comprising an effective amount of angiotensin-(1-9) or derivatives thereof and at least one pharmaceutically acceptable carrier, excipient, stabilizer, diluent and/or adjuvant. Furthermore, said invention describes the use of the pharmaceutical composition and the peptide angiotensin-(1-9) or peptides derived therefrom, which are biological or chemical analogs, to produce medicaments useful for preventing, reversing, inhibiting and/or reducing cardiovascular, pulmonary, renal or cerebral remodeling. Moreover, the applications CL3736-2008 and PCT/CL2009000029 also comprise a method for preventing, reversing, inhibiting and/or reducing cardiovascular, pulmonary, cerebral or renal remodeling, consisting in increasing the concentration in the blood and/or tissues of the peptide angiotensin-(1-9) or derivatives thereof using a pharmaceutical composition containing a vector expressing ACE2, which is the enzyme responsible for endogenously producing angiotensin-(1-9). These vectors correspond to adenovirus, retrovirus, lentivirus and adeno-associated virus containing the gene encoding for ACE2. The applications CL3736-2008 and PCT/CL2009000029 allow the administration of angiotensin-(1-9) or derivatives thereof in oral form, injectable form, continuous infusion via pump, or the increase of its levels in the body by means of a treatment with ACE inhibitors, with angiotensin II receptor antagonists (ARA II), with Rho kinase inhibitors with antagonists of the L-type calcium channels and/or with diuretics.

However, the state of art describes neither the biological effects for the peptide angiotensin-(1-9) on the control of blood pressure and/or control of vascular dilation, nor the medical uses of angiotensin-(1-9) and/or derivatives thereof in medicine, particularly in the treatment of hypertension, nor as an agent to induce vasodilation. The present invention solves the technical problem related to the lack of knowledge about the activity of angiotensin-(1-9) on blood pressure and/or vasodilation, and it describes the antihypertensive and/or vasodilator effects of this peptide, providing methods for increasing the plasma and/or tissue concentration of angiotensin-(1-9).

DETAILED DESCRIPTION OF THE INVENTION

There are several methods for increasing the plasma and/or tissue concentration of angiotensin-(1-9). Elevated plasma and/or tissue levels of angiotensin-(1-9) are associated with phenomena of reduction in blood pressure and/or induction of vasodilation. In the present invention it is described that such elevated plasma concentration of angiotensin-(1-9) can be achieved through:

a) Administration of the peptide angiotensin-(1-9) (see Examples 1, 4 and 5).

b) Administration of a gene overexpressing the homologue angiotensin-I-converting enzyme (ACE2), which is the enzyme responsible for the endogenous production of angiotensin-(1-9) (see Examples 6, 7 and 8).

The present invention corresponds to a pharmaceutical composition comprising an effective amount of angiotensin-(1-9) or derivatives thereof and at least one pharmaceutically acceptable carrier, excipient, stabilizer, diluent and/or adjuvant. The present invention also describes the use of said pharmaceutical composition for the production of medicaments useful for preventing, reversing, inhibiting and/or reducing hypertension and/or inducing vasodilation. Furthermore, the present invention discloses the use of the peptide angiotensin-(1-9) or derivatives thereof for producing medicaments and/or pharmaceutical compositions useful for preventing, reversing, inhibiting and/or reducing hypertension and/or inducing vasodilation, especially in animals or humans, more especially in patients needing such treatment, and even more specifically in patients suffering from hypertension. The present invention also provides, through the use of angiotensin-(1-9) and/or derivatives, a method for preventing, reversing, inhibiting and/or reducing hypertension and/or inducing vasodilation.

Furthermore, this invention also comprises a method for preventing, reversing, inhibiting and/or reducing hypertension and/or inducing vasodilation, which consists in increasing the concentration in the blood and/or tissues of the peptide angiotensin-(1-9) or derivatives thereof by means of a pharmaceutical composition containing a vector expressing ACE2, which is the enzyme responsible for the endogenous production of angiotensin-(1-9). These vectors are adenovirus, retrovirus, lentivirus and adeno-associated virus containing the gene encoding for ACE2.

According to the invention, the method for preventing, reversing, inhibiting and/or reducing hypertension and/or inducing vasodilation in a human or an animal comprises administering to the patient an effective amount of angiotensin-(1-9) and/or at least one angiotensin-(1-9) derivative. The present invention also provides a pharmaceutical composition comprising an effective amount of angiotensin-(1-9) and/or at least one angiotensin-(1-9) derivative and, at least, one pharmaceutically acceptable excipient, carrier, diluent, stabilizer and/or adjuvant. The composition is preferably for use in the prevention, reversal, inhibition and/or reduction of hypertension and/or induction of vasodilation in a human or an animal in need of such treatment, and it comprises administering to the patient such a pharmaceutical composition. The patient may be human or animal. In particular, said patient is a hypertensive human or animal. The use of said medicament or pharmaceutical composition aims to increase plasma and/or tissue levels of angiotensin-(1-9) and/or, at least, one of the derivatives thereof. It particularly seeks to increase the levels of said peptides in the body, particularly in the plasma and/or vascular bed.

The medicament or pharmaceutical composition of the present invention, containing an effective amount of angiotensin-(1-9) and/or at least one angiotensin-(1-9) derivative, can be applied through all known routes of drug administration described. In particular, said medicament or pharmaceutical composition will be applied by injection and/or via parenteral route (non-limiting examples of said routes are intravenous, intra-arterial, intramuscular, intraperitoneal, intradermal, subcutaneous, and inhalation routes, using continuous release pharmaceutical compositions, using pumps for continuous release, suppositories, and oral route). Said administration may be a single dose, multiple dose, or continuous administration.

The angiotensin-(1-9) and/or derivatives thereof, pharmaceutical compositions containing it/them and/or medicaments containing it/them according to the present invention may be in solid or liquid form, including tablets, cachets, lozenges, pills, capsules, suspensions, or solutions, containing at least one pharmaceutically acceptable excipient, carrier, diluent, stabilizer and/or adjuvant. Pharmaceutically acceptable excipients, carriers, diluents, stabilizers and/or adjuvants for the preparation of pharmaceutical compositions or medicaments of the invention are well known in the art, and may be in solid or liquid form, or mixtures of both. Thus, the pharmaceutical compositions or medicaments can be in the form of tablets, pills, capsules, lozenges, cachets, powders, coated formulations, sustained release formulations, erodible formulations, implanted devices or components derived from such apparatus, microsphere formulations, solutions, suspensions, elixirs, sprays and the like, among others. Preferred carriers, diluents and/or liquid carriers are water, saline, dextrose solution, and glycol solution, especially when the administration route is parenteral and/or injection. The carrier and/or diluent can also be oil, such as those derived from petroleum, oils of animal and/or vegetable origin, or synthetic oils. Particular examples of the preferred oils in the invention include peanut oil, soybean oil, mineral oil, sesame oil, corn oil, sunflower oil, among others. The preferred excipients of the invention include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, among others. Other carriers, diluents, stabilizers, excipients and/or adjuvants, which are not listed here, are obvious to the person skilled in the art. The composition or medicament of the present invention may be subjected to conventional pharmaceutical processes, such as sterilization, and may contain other conventional pharmaceutical additives, such as preservatives, stabilizers, emulsifying agents, wetting agents, salts for adjusting osmotic pressure, or buffers for pH adjustment, among others. Carriers, stabilizers, diluents, excipients and/or adjuvants and their formulations can be found in Martin, "Remington's Pharmaceutical Sciences", $15^{th}$ Ed.; Mack Publishing Co., Easton (1975); see for instance pages 1405-1412 and 1461-1487. Said compositions generally contain an effective amount of the active compound together with a suitable amount of one or more carriers, stabilizers, diluents, excipients and/or adjuvants so as to enable the preparation of the dose and the form suitable for the proper administration of angiotensin-(1-9) and/or derivatives thereof to the patient. In the practice, in the treatment methods of the invention, the particular dosage of a pharmaceutical composition or a medicament to be administered to the subject will depend on several variables, which include the status of the disease, the severity of the disease, the schedule of administration, age, physical characteristics of the subject, etc. The appropriate doses can be established using clinical approximations known by the experts in the field.

Moreover, angiotensin-(1-9) and/or at least one of the derivatives thereof, the medicament or the pharmaceutical composition of the present invention can be administered together with at least one pharmaceutical compound. The "at least one pharmaceutical compound" is an inhibitor of the angiotensin-I-converting enzyme, an antagonist of the angiotensin II receptor (ATR1), an antagonist of L-type calcium channels, an inhibitor of Rho kinase, a renin inhibitor and/or a diuretic. The administration of any of these pharmaceutical compounds can increase per se the plasma concentration of angiotensin-(1-9). It was previously described that in the Chilean patent application CL3736-2008 and the international patent application PCT/CL2009000029, and in Ocaranza et al., Hypertension 48:572-8, 2006, and in Ocaranza et al., Rev. Chil. Cardiol. 26:63-76, 2007, the administration of a converting enzyme inhibitor (enalapril), or the administration of an antagonist of the angiotensin II receptor (candesartan) increase plasma and/or tissue levels of angiotensin-(1-9).

Examples of inhibitors of the angiotensin-I-converting enzyme (ACE) include lisinopril, enalapril, captopril, zofenopril, ramipril, quinapril, perindopril, benazepril, and fosinopril. Examples of antagonists of the angiotensin II receptor (ATR1) are valsartan, telmisartan, losartan, irbesartan, olmesartan, candesartan, eprosartan and saralasin. Examples of antagonists of L-type calcium channels are dihydropyridines (nicardipine, nifedipine, amlodipine, felodipine, nitrendipine, nisoldipine, isradipine, nimodipine), benzothiazepines (diltiazem, clentiazem), and phenylalkylamines (verapamil, gallopamil, anipamil, RO5967, falipamil). Examples of Rho kinase inhibitors are fasudil, hydroxyfasudil, 3-(4-pyridyl)-1H-indole, (S)-(+)-2-methyl-1-[(4-methyl-5-isoquinolinyl)sulfonyl]homopiperazine, N-(4-pyridyl)-N'-(2,4,6-trichlorophenyl)urea. Examples of renin inhibitors are Aliskiren and Remikiren. Examples of diuretics are thiazide diuretics (bendroflumethiazide, benzithiazide, chlorothiazide, chlorthalidone, hydrochlorothiazide, hydroflumethiazide, indapamide, methyclothiazide, metolazone, polythiazide, quinethazone, trichlormethiazide, xipamide), loop diuretics (furosemide, torasemide, bumetanide, ethacrynic acid), carbonic anhydrase inhibitor diuretics (acetazolamide, dorzolamide), potassium-saving diuretics, which are sodium channels inhibitors (amiloride, triamterene), potassium-saving diuretics, which are aldosterone antagonists (spironolactone, canrenoate, eplerenone), and osmotic diuretics (mannitol).

The present invention also considers as part of the invention increasing the plasma and/or tissue levels of angiotensin-(1-9) by increasing its production and/or inhibiting its degradation. Additionally, the present invention involves exacerbation, activation, and/or induction of intracellular transduction signals activated by angiotensin-(1-9) and/or derivatives thereof.

The increased production of angiotensin-(1-9) and/or derivatives thereof can be achieved by increasing or overexpressing ACE2. The increased activity of ACE2 can be achieved by inhibiting ACE, specifically, with the use of inhibitors of this enzyme, particularly drugs which are already known in the art, such as lisinopril, enalapril, captopril, zofenopril, ramipril, quinapril, perindopril, benazepril and fosinopril. The overexpression of ACE2 can be achieved by introducing one or several copies of the ACE2-encoding gene into the organism. The introduction of the gene encoding for ACE2 into the organism is achieved by techniques already described in the art including naked DNA, liposomes (particularly cationic liposomes) and by the use of viral vectors. In the present invention, it is more particularly described, without limitation as to any other viral vectors, the use of adenoviral, retroviral, lentiviral vectors and adeno-associated virus containing the ACE2-encoding gene within its genetic material. It is also known by those skilled in the art that for such gene to be active it requires that its expression be commanded by a promoter and that the gene ends at a terminator. The aforementioned vectors of this patent include flanking the gene encoding for ACE2, a promoter and a terminator. It is also part of the present invention that vectors containing the gene encoding for ACE2 have DNA sequences which are important to enhance mRNA stability, as well as sequences which allow normal transduction of mRNA into protein. Likewise, several promoter structures that allow constitutive or regulated expression of the desired genes are well known in the art. The present invention also considers that the promoter regulating the expression of the ACE2-encoding gene be constitutive or regulated in nature by means of gene induction or repression.

In the present invention angiotensin-(1-9) is used as an example of angiotensin-(1-9) and/or derivatives thereof. Moreover, rat is used as an example of mammal to which the treatment method can be applied and upon which the use of angiotensin-(1-9) and/or derivatives thereof as a medicament and/or pharmaceutical composition can be tested. Animal models to study blood pressure and vasodilation, including small mammals, such as rats, are very well accepted in the art (Pinto et al. Cardiovasc. Res. 39:77-88, 1998). Using the rat model does not preclude its use in humans or other animal requiring such treatment.

In the present invention the term blood pressure is understood as the abnormal increase in blood pressure. The abnormal increase in blood pressure in humans corresponds to systolic pressures equal to or greater than 90 mm Hg and/or 140 mm Hg. The increase in systolic and diastolic blood pressure may be due to an increase in cardiac output or an increased peripheral resistance. The increase in cardiac output may be due to an increased heart rate and/or an increased cardiac stroke volume. The stroke volume is the volume of blood ejected by the ventricle (right or left equally) in one cardiac cycle; in a healthy heart it corresponds to an electric cycle and a mechanical cycle, synchronized. Heart rate is the number of cardiac cycles in a minute. The stroke fraction, in turn, depends on two factors: mechanical and afterload activity. The mechanical activity of the heart depends on the force of contraction (which according to the Frank-Starling law is proportional to the end-diastolic volume) and contractility. The afterload is the force that opposes the outflow of blood from the ventricle during systole; or it may be defined as the degree of stress in the wall of the ventricle during ventricular systole.

The increased peripheral resistance may be due to an increased blood volume, an increased blood viscosity and/or a decreased caliber of blood vessels. The resistance to the blood flow is determined by the vascular smooth muscle tone and the caliber of blood vessels.

Vasodilation is the ability of the blood vessels (arteries and veins) to dilate (increasing the caliber) in front of chemical stimuli secreted by inflammatory cells, endothelium (nitric oxide), nerve afferents or drugs. This causes a decrease in blood pressure when it occurs in the arterial area.

An effective amount refers to the dose of angiotensin (1-9) and the period of time necessary to achieve the necessary therapeutic result, i.e. prevent, reverse, inhibit and/or reduce hypertension and/or inducing vasodilation. The effective amount may depend on many factors such as the progress of the disease, age, sex, weight of the individual, the presence of other diseases, the intake of other drugs simultaneously, race, between other things. In this patent, the invention seeks to lift the tissue plasma and/or inhibitor (1 9) to greater than 10 fmol/g values, more particularly greater than 20 fmol/g values, more specifically to values above 40 fmol/g, and even more specifically greater than 80 fmol/g values.

An angiotensin-(1-9) derivative is any mutation, fragment, part or portion of the angiotensin-(1-9) which includes molecules with substitution, deletion and/or insertion of one or more amino acids into the angiotensin-(1-9) in order to mimic its biological effect and/or physiological effect, to favor its biological and/or physiological effect, to increase its biological and/or physiological effect, to increase its bioavailability, to increase its stability, to increase its absorption, to increase its plasma and/or tissue half-life, to alter its binding to plasma proteins, to increase its affinity to its receptor, to reduce its degradation, or any other biological, physiological, pharmacological and/or pharmaceutical property that is of interest to improve its therapeutic action. The angiotensin-(1-9) derivatives obtained from the substitution of amino acids correspond to the substitution of an amino acid by another amino acid or by another molecule which can correspond to an amino acid derivative. In this case, the aim is to obtain a derivative that is functionally, structurally and stereochemically similar or homologous to angiotensin-(1-9). Angiotensin-(1-9) derivatives also include mimotopes, or peptides, or mimetic analogs, and include molecules containing unnatural amino acids, as well as molecules which do not correspond to amino acids, but which behave or function and/or exhibit activities similar to amino acids. Angiotensin-(1-9) derivatives also include modifications such as glycosylations, amidations, acetylations, hydroxylations, methylations, ethylations, esterifications, etc., which in general are modifications of the side chains of amino acids or molecules that are part of the angiotensin-(1-9) or derivatives thereof. It is also considered as part of an angiotensin-(1-9) derivative the introduction of crosslinking molecules that allow binding this peptide to a larger structure to help with its physicochemical and/or pharmaceutical properties. The crosslinking molecule can have different chain lengths so as to move angiotensin-(1-9) or the derivatives thereof closer to or away from the larger molecule. The crosslinkers can be homo or bifunctional, such as bifunctional imido esters having a methyl group as spacers between n=1 to 6 of chain length, glutaraldehyde, N-hydroxysuccinimide esters and hetero-bifunctional reagents, which usually contain an amino-reactive part, such as N-hydroxysuccinimide, and another part that is reactive specifically to another functional group or to the same functional group. Angiotensin-(1-9) derivatives may also correspond to chemically modified derivatives to help stabilize a three-dimensional structure so as to be more favorable to mimic its biological and/or physiological effect, to promote its biological and/or physiological effect, to increase its biological and/or physiological effect, to increase its bioavailability, to increase its stability, to increase its absorption, to increase its plasma and/or tissue half-life, to alter its binding to plasma proteins, to increase its affinity to its receptor, to decrease its degradation, or any other biological, physiological, pharmacological and/or pharmaceutical property that is of interest to improve its therapeutic action.

Examples of unconventional or unnatural amino acids and/or the derivatives thereof which can be incorporated during peptide synthesis include the use of, but are not limited to, norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. Other examples of unconventional or unnatural amino acids and/or the derivatives thereof are α-amino-α-methyl-butyrate acid, cyclopentylalanine, aminocyclopropane-carboxylic acid, cyclohexylalanine, aminoisobutyric acid, aminonorbornyl-carboxylic acid, D-alanine, D-arginine, D-aspartic acid, D-cysteine, D-glutamine, D-glutamic acid, D-histidine, D-isoleucine, D-leucine, D-lysine, D-methionine, D-ornithine, D-phenylalanine, D-proline, L-N-methylalanine, L-N-methylarginine, L-N-methylasparagine, L-N-methylaspartic acid, L-N-methylcysteine, L-N-methylglutamine, L-N-methylglutamic acid, cyclohexyl L-N-methylhistidine, L-N-methylisoleucine, L-N-methylleucine, L-N-methyllysine, L-N-methylmethionine, L-N-methylnorleucine, L-N-methylnorvaline, L-N-methylornithine, L-N-methylphenylalanine, L-N-methylproline, L-N-methylserine, L-N-methylthreonine, L-N-methyltryptophan, L-N-methyltyrosine, L-N-methylvaline, L-N-methylethylglycine, D-serine, D-threonine, D-tryptophan, D-tyrosine, D-valine, D-α-methylalanine, D-N-methylarginine, D-N-methylasparagine, D-α-methylaspartate, D-α-methylcysteine, D-α-methylglutamine, D-α-methylhistidine, D-α-methylisoleucine, D-α-methylleucine, D-α-methyllysine, D-α-methylmethionine, D-α-methylornithine, D-α-methylphenylalanine, D-α-methylproline, D-α-methylserine, D-α-methylthreonine, D-α-methyltryptophan, D-α-methyltyrosine, D-α-methylvaline, D-N-methylalanine, D-N-methylarginine, DN-methylasparagine, D-N-methylaspartate, D-N-methylcysteine, D-N-methylglutamine, D-N-methylglutamate, D-N-methylhistidine, D-N-methylisoleucine, D-N-methylleucine, L-N-methyl-t-butylglycine, L-norleucine, L-norvaline, α-methyl-aminoisobutyrate, α-methyl-α-aminobutyrate, α-methylcyclohexylalanine, α-methylcyclopentylalanine, α-methyl-α-napthylalanine, α-methylpenicillamine, N-(4-aminobutyl)glycine, N-(2-aminoethyl)glycine, N-(3-aminopropyl)glycine, N-amino-α-methylbutyrate, α-naphthylalanine, N-benzylglycine, N-(2-carbamylethyl)glycine, N-(carbamylmethyl)glycine, N-(2-carboxyethyl)glycine, N-(carboxymethyl)glycine, N-cyclobutylglycine, N-cycloheptylglycine, N-cyclohexylglycine, N-cyclodecylglycine, N-cyclododecylglycine, N-cyclooctylglycine, N-cyclopropylglycine, N-cycloundecylglycine, N-(2,2-diphenyiethyi)glycine, N-(3,3-diphenylpropyl)glycine, N-(3-guanidinopropyl)glycine, N-(1-hydroxyethyl)glycine, N-(hydroxyethyl)glycine, N-(imidazolylethyl)glycine, N-(3-indolylethyl)glycine, D-N-methyllysine, N-methylcyclohexylalanine, D-N-methylornithine, N-methylglycine, N-methylaminoisobutyrate, N-(1-methylpropyl)glycine, N-(2-methylpropyl)glycine, D-N-methyltryptophan, D-N-methyltyrosine, D-N-methylvaline, α-aminobutyric acid, L-t-butylglycine, L-ethylglycine, L-homophenylalanine, L-methylarginine, L-methylaspartate, L-methylcysteine, L-methylglutamine, L-methylhistidine, L-methylisoleucine, L-methylleucine, L-methylmethionine, L-methylnorvaline, L-methylphenylalanine, L-methylserine, L-methyltryptophan, L-methylvaline, N—(N-(2,2-diphenylethyl)carbamylmethyl)glycine, 1-carboxy-1-(2,2-diphenyl-ethylamino)cyclopropane, N-methyl-α-aminobutyrate, D-N-methylmethionine, N-methylcyclopentylalanine, D-N-methylphenylalanine, D-N-methylproline, D-N-methylserine, D-N-methylthreonine, N-(1-methylethyl)glycine, N-methyl-α-naphthylalanine, N-methylpenicillamine, N-(p-hydroxyphenyl)glycine, N-(thiomethyl)glycine, penicillamine, L-N-methylalanine, L-α-methylasparagine, L-α-methyl-t-butylglycine, L-methylethylglycine, L-α-methylglutamate, L-α-methylhomophenylalanine, N-(2-methylthioethyl)glycine, L-α-methyllysine, L-α-methylnorleucine, L-α-methylornithine, L-α-methylproline, L-α-methylthreonine, L-α-methyltyrosine, L-N-methylhomophenylalanine, and N—(N-(3,3-diphenylpropyl)carbamylmethyl)glycine.

As described above, an angiotensin-(1-9) chemical analogue and/or homologue share certain conformational and/or functional similarities, but it is not necessarily derived from angiotensin-(1-9). Thus, a chemical equivalent may be designed to mimic certain biological and/or physiological properties of angiotensin-(1-9).

Although in the present invention the use of angiotensin-(1-9) and/or the derivatives thereof and medicaments, or pharmaceutical compositions containing it/them in rats is particularly exemplified, it is understood that the present invention extends to the use of the angiotensin-(1-9) and/or the derivatives thereof and medicaments, or pharmaceutical compositions containing it/them according to the invention in any mammal including, but not limited to, humans, mice, rabbits, primates, dogs, cats, pets, livestock animals, etc.

DESCRIPTION OF THE FIGURES

The patent or application file contains at least one color drawing. Copies of this patent or patent application publication with color drawing will be provided by the USPTO upon request and payment of the necessary fee.

EXAMPLES

Example 1

Experimental Design and Animals

Figure 1:
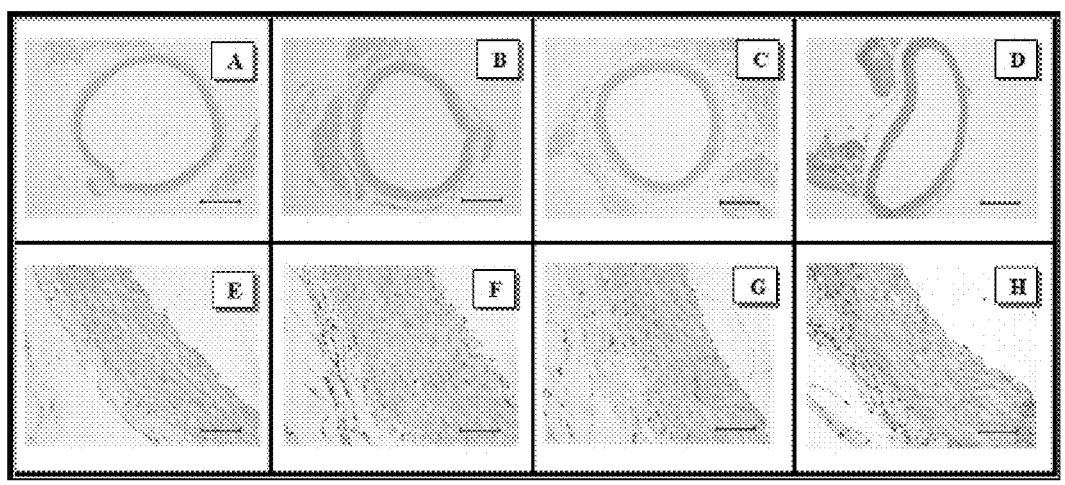
FIG. 1. Preventive effect of the angiotensin-(1-9) in the hypertrophy of the aortic wall of hypertensive rats due to administration of angiotensin II. Cross sections, panels A, B, C and D (4x) and E, F, G and H (40x) of thoracic aortas of Sham animals (A and E), angiotensin II (B and F), angiotensin II/1-9 (C and G) and angiotensin II/1-9/A779 (D and H). Top bar: 0.5 mm, and bottom bar: 50 μm.

Male Sprague-Dawley normotensive rats of 200±10 g, obtained from the Central Animal Facility, Pontificia Universidad Católica de Chile (PUC) were used. The experiments were performed according to the "Guide for the Care and Use of Laboratory Animals" (NIH No. 85-23, 1985) and were approved by the Committee on Animal Care and Welfare, Faculty of Medicine, Pontificia Universidad Católica de Chile.

1. Experimental Design of a Model of Hypertension Induced by Angiotensin II Infusion.

Rats were subjected to the model of angiotensin II infusion (Grobe et al.: Am. J. Physiol. 292: H736-42, 2007). The animals were separated randomly into the following experimental groups: controls (Sham or pseudo-operated), infused with angiotensin II (300 ng/kg min), infused with angiotensin II and angiotensin-(1-9) (300 ng/kg min and 602 ng/kg min, respectively), and then infused with angiotensin II, angiotensin-(1-9) and the angiotensin-(1-7) receptor antagonist, A779 (300 ng/kg min, 602 ng/kg min, and 100 ng/kg min, respectively). In all cases the pumps operated at a flow of 0.5 μL/h and were implanted in the right jugular vein through a catheter fitted in an intrascapular subcutaneous pocket under anesthesia with ketamine HCl/xylazine (35 and 7 mg/kg i.p., respectively), for a period of 14 days.

2. Experimental Design of a Model of Hypertension by Renal Artery Clamping (Goldblatt Procedure, GB, 2 Kidneys, 1 Pinch).

Lewis normotensive rats (weight 150±10 g), which were separated randomly into the experimental hypertension model group or GB (Ocaranza et al. J. Hypertens. 20:413-20, 2002) or control group (S) were used. The latter corresponded to pseudo-operated animals. All animals were maintained under controlled conditions of light and darkness and had free access to food and water. Four weeks after surgery and at a blood pressure above 140 mmHg, GB rats were randomized for the chronic administration of angiotensin-(1-9) through an osmotic pump (602 ng kg$^{-1}$min$^{-1}$) via the jugular vein during two weeks. The animals were euthanized after 6 weeks post-surgery.

3. Statistical Analysis

The experimental groups were composed by 6-12 rats. Data were expressed as mean±S.E.M. For comparisons a statistical analysis with ANOVA followed by Student-Newman-Keuls t test were used. The statistical analysis was performed using the statistical package SPSS 10.0. A value of p<0.05 is considered as statistically significant.

Example 2

Hemodynamic and Functional Studies

Systolic blood pressure (SBP) was measured by the tail plethysmographic method in the animals. To such end, rats were lightly anesthetized with ethyl ether. The measurement was performed once a week by researchers blind to the treatment (Ocaranza et al. J. Hypertens. 20:413-20, 2002).

Example 3

Evaluation of Cardiac and Vascular Remodeling

1. Evaluation of Cardiac Hypertrophy

The degree of cardiac hypertrophy (CH) was measured by the ratio of the cardiac mass (CM), the body mass (BM) and relative cardiac mass (RCM; [CM/BM]*100) (Ocaranza et al., J. Hypertens. 28:1054-1064, 2010).

2. Evaluation of Aortic Hypertrophy

Aortic hypertrophy was determined by morphometry. Sections of the descending aorta of 5 μm thick, which were previously fixed in Bouin (1.3% picric acid, 9.5% formaldehyde and 4.8% acetic acid) for 24 hours, embedded in paraffin and stained with hematoxylin-eosin, were used, to be examined later in a light microscope as described by Igase et al. (Am. J. Physiol. 289:H1013-9, 2005). Briefly, images of the aortas were captured by a video camera (Nikon) fixed to a microscope (Nikon), and projected on a monitor; using the software Nis-Element. Lumen areas (LA) and total areas (TA) were calculated and recorded. The tunica media area (TMA) was obtained from the difference between the TA and LA of the aorta. The tunica media thickness (TMT) was defined as the region delimited by the external elastic lamina (EEL) and internal elastic lamina (IEL).

3. Morphological and Morphometric Analyses of Cardiac Tissue

The middle portion of the left ventricle (LV) was dehydrated at room temperature for 24 h in Bouin and then embedded in paraffin. Sections of 10-15 μm thick were taken and stained with hematoxylin-eosin, to be examined later in a light microscope in order to observe their general morphological characteristics. Cardiomyocyte size was determined according to Nakamura et al. (Circulation, 98:794-9, 1998). Briefly, images of the cells were captured using a Nikon DS Fi1 camera and projected on a monitor using a software program. The cardiomyocyte area and perimeter were measured and recorded, using the Nis-Element program (Ocaranza et al. J. Hypertens., 28:1054-64, 2010). All measurements were performed by a blinded observer, and at least 80 images of cells per animal, which were randomly selected, were analyzed.

4. Morphometric Evaluation of the Development of Cardiac Fibrosis

Sections of 5 μm of ventricle, previously included in Bouin, which were treated with picrosirius red, were used. The tissue was examined under light microscopy, images were captured with a Nikon DS Fi1 camera and projected on a monitor. The Matlab program was used to measure the interstitial collagen content according to the procedure described by Ocaranza et al. (J. Cardiovasc. Pharmacol. 40:246-54, 2002).

5. Evaluation of Inflammation of the Aorta through TGF-β and MCP-1 mRNA Levels

The procedure described by Ocaranza et al. (Hypertension 48:572-8, 2006) was followed. Briefly, total RNA was isolated from the aorta using the trizol method and quantified by spectroscopy at 260 nm/280 nm. The cDNA was obtained by reverse transcription from 1.5 μg of total RNA treated with DNAse. PCR assays were performed using the following amplification protocols and primer sequences (Ocaranza et al. J. Cardiovasc. Pharmacol. 40:246-54, 2004), TGFβ1 33 cycles of denaturation at 94° C. for 1 min, hybridization at 52° C. for 1 min and elongation at 72° C. for 1 min. 5'-AAGCCCTGTATTCCGTCTCC-3' was used as sense primer, and 5'-CAACGCCATCTATGAGAAAACC-3' as antisense primer. MCP-1 38 cycles of 1 min at 92° C., 1 min at 53° C., 1 min at 72° C. and then 10 min at 72° C. The nucleotide sequences of the sense and antisense primers were 5'-CAGGTCTCTGTCACGCTTCT-3' and 5'-GTGCTTCAGGTGGTTGTGG-3', respectively. The band intensity was quantified by densitometry and normalized to the 18S ribosomal RNA band.

6. Protein Levels of Collagen I and TGFβ-1

For the determination of collagen I and TGFβ-1, 30 μg and 50 μg of total proteins were used, respectively, diluted in SDS reducing buffer (50 mM tris-HCl, pH 7.4, NP-40 10%, NaCl 1M, Na deoxycholate 5%, EDTA 10 mg/mL, SDS 10%, aprotinin 1 mg/mL, leupeptin 0.1 mg/mL, PMSF 10 mM), they were then separated by SDS-PAGE gel electrophoresis 7%, and transferred to nitrocellulose membranes of 0.2 μg to 300 mA for 1 h. The transfer of proteins was monitored by Ponceau red staining. Subsequently, the membranes were blocked in a solution 7% of skimmed milk/PBS-Tween 20 0.05% during 1.30 h at room temperature and after 3 washes of 10 min with wash buffer (milk 0.5% in PBS-Tween 20 0.05%), incubated overnight with anti-collagen I antibody (1:3000 dilution) or anti TGF6-1 (1:2500 dilution) in wash solution with constant stirring at 4° C. After 3 washes of 10 min with wash solution, the anti-rabbit secondary antibody in 1:10000 dilution was added and incubated for 2 h at room temperature. Finally, after 3 washes a chemiluminescent substrate was revealed for subsequent quantification of the intensity of bands by densitometry (Ocaranza et al. J. Cardiovasc. Pharmacol. 40:246-54, 2004).

7. Immunohistochemistry for Determination of Inflammatory Cells (ED-1)

Immunostaining was performed using the streptavidin-biotin-peroxidase method with the inflammation marker ED-1. This is a glycoprotein expressed primarily in the lysosomal membrane of active macrophages (Leskovar et al. J. Exp. Biol. 203:1783-1795, 2000).

In order to block endogenous peroxidase, the samples were deparaffinized, rehydrated and treated with 10% $H_2O_2$ in methanol for 1 h. Then, the tissues were incubated with monoclonal antibody anti ED-1 (clone MCA341R, Serotec) diluted 1/1000 in 1% BSA prepared in PBS-0.05% Tween 20 overnight at 4° C. in a humid chamber. The sections were washed three times with 1×PBS-0.05% Tween 20, pH 7.4 for 5 min and incubated with the biotinylated secondary antibody for 30 min at room temperature. Then the tissues were washed again and incubated with the streptavidin-peroxidase complex for 30 min at room temperature. The immunoreactive sites were visualized with 3,3'-diaminobenzidine. The slides were counter-stained with hematoxylin, dehydrated, cleared in xylene and mounted with Permaunt (Fisher).

Example 4

Angiotensin-(1-9) Prevents the Increase in Blood Pressure and Vascular Remodeling Induced by Angiotensin II Infusion 1. Experimental Groups Four experimental groups of rats were established as described in Example 1. Group 1 corresponds to rats which were infused with saline (Sham). Group 2 corresponds to rats which were infused with only angiotensin II. Group 3 correspond to rats which were co-infused with angiotensin II and angiotensin-(1-9). And Group 4 corresponds to rats which were co-infused with angiotensin II, angiotensin-(1-9) and A779.

2. Systolic Blood Pressure

There was no significant difference in the body mass (BM) of the 4 experimental groups. However, the CM and the RCM were lower for the rats infused with angiotensin II vs. the rats infused with angiotensin II/1-9, angiotensin II/1-9/A779 and Sham. SBP was significantly higher (13%) in the rats infused with angiotensin II over the rats infused with angiotensin-(1-9)+A779. In the case of the co-administration of angiotensin-(1-9) or angiotensin-(1-9)+A779 decreased in the same manner the SBP as compared to angiotensin II (—10% and 13%, respectively, Table 1).

TABLE 1

Effect of angiotensin-(1-9) in body weight, cardiac mass and systolic blood pressure of hypertensive rats by administration of angiotensin II

| Parameter | Sham (n = 12) | Ang II (n = 12) | Ang II/1-9 (n = 12) | AngII/1-9/A779 (n = 9) |
|---|---|---|---|---|
| BM (g) | 280 ± 19 | 260 ± 25 | 255 ± 24 | 279 ± 28 |
| CM (mg) | 938 ± 16 | 899 ± 28 | 984 ± 26*# | 1042 ± 34*# |
| RCM (MV/MC) | 332 ± 17 | 348 ± 18* | 386 ± 36# | 377 ± 33# |
| Initial SBP | 119 ± 9 | 121 ± 9 | 123 ± 11 | 121 ± 5 |
| SBP $1^{st}$ week | 116 ± 10 | 130 ± 4* | 141 ± 9*# | 139 ± 5*# |
| SBP $2^{nd}$ week | 118 ± 8 | 154 ± 10* | 139 ± 11*# | 135 ± 9*# |

Figure 2:
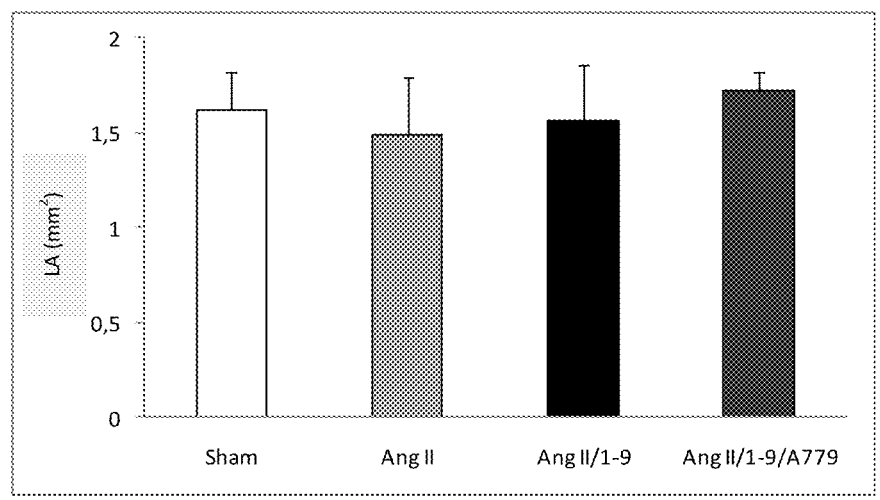
FIG. 2. Effect of the continuous administration of angiotensin-(1-9) on the luminal area of thoracic aortas of hypertensive rats by angiotensin II infusion. The values represent the mean±SEM. N=9-12.
Figure 3:
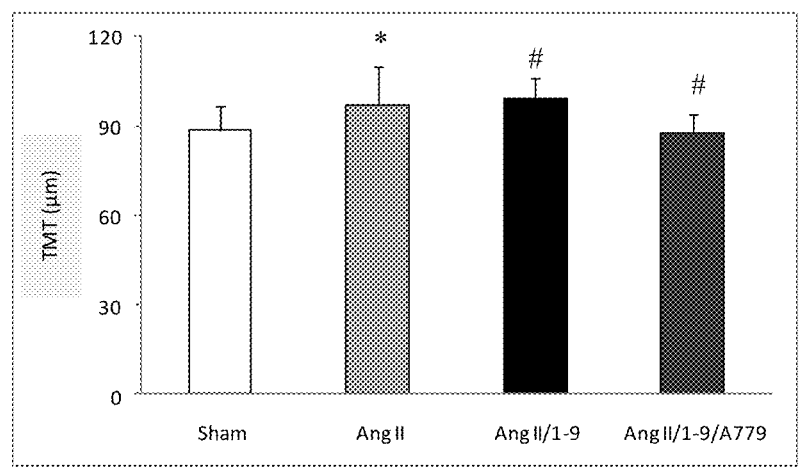
FIG. 3. Effect of the continuous administration of angiotensin-(1-9) on the thickness of the tunica media of hypertensive rats by angiotensin II infusion. The values represent the mean±SEM. $^\#p<0.05$ vs. angiotensin II, $*p<0.05$ vs. Sham (after ANOVA). N=9-12.
Figure 4:
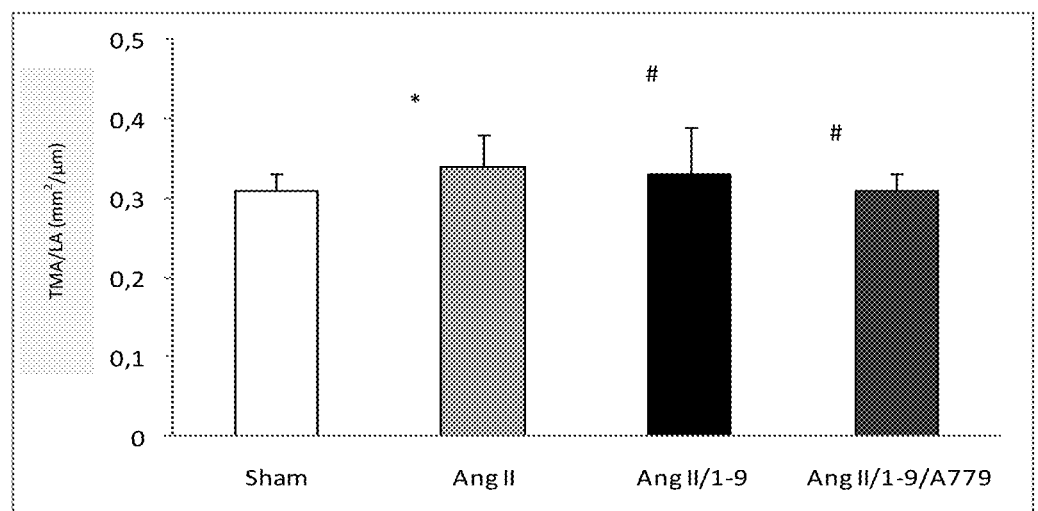
FIG. 4. Effect of the continuous administration of angiotensin-(1-9) on the TMA/LA of the aortic wall of hypertensive rats by angiotensin II infusion. The values represent the mean±SEM. $^\#<0.05$ vs. Ang II, $*p<0.05$ vs. Sham (after ANOVA). N=9-12.

Hypertension was defined as the mean systolic blood pressure of Sham rats+SDS=141 mmHg. The results represent the mean±SEM. *$p<0.05$ vs. Sham, #$p<0.05$ vs. angiotensin II (after significant ANOVA). Abbreviations: Ang=angiotensin, BM=body mass, CM=cardiac mass, LV=left ventricle, RCM=relative cardiac mass, SBP=systolic blood pressure 3. Vascular Hypertrophy Hypertension induced by angiotensin II infusion increased significantly the thickness of the tunica media (TMT) (FIGS. 1 and 3), with no change in the vascular lumen area (LA) (FIG. 2). An increase in the ratio of tunica media area (TMA) to LA (FIG. 4) in rats with angiotensin II as compared to the control rats was observed (FIGS. 1B and 1F vs. FIGS. 1A and 1E). Confusion with angiotensin-(1-9) significantly prevented the increase in TMT (FIG. 3) and in TMA/LA induced by angiotensin II infusion (FIG. 4). This effect was not affected by the administration of A779 (FIGS. 1D, 1H, 3 and 4). No differences in LA between the different experimental groups were observed (FIG. 2).

Figure 5:
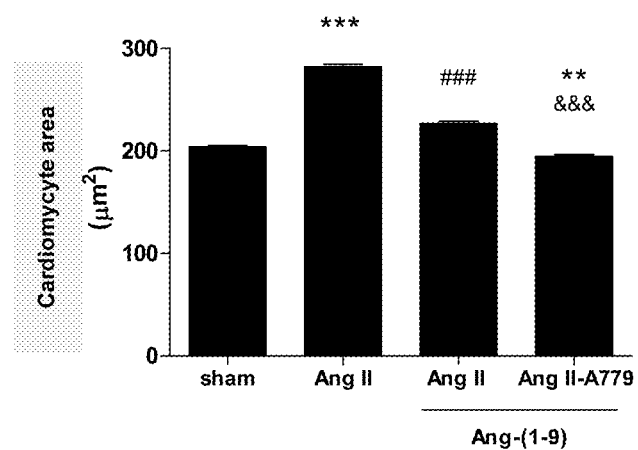
FIG. 5. Effect of angiotensin-(1-9) in cardiomyocyte hypertrophy induced by Ang II in vivo. Male normotensive rats were randomized to receive angiotensin II in the presence or absence of angiotensin-(1-9) and A779 for two weeks. A. Microphotograph of a cross section of left ventricle stained with hematoxylin and eosin (400x). Scale bar, 50 μm. B. Quantification of cardiomyocyte area, and C. Quantification of cardiomyocyte perimeter. The results are presented as mean±SEM (n=9-12). $***p<0.001$ vs. Sham; $^{\#\#\#}p<0.001$ vs. angiotensin II, $^{\&\&\&}p<0.001$ vs. angiotensin II+angiotensin-(1-9) (after significant ANOVA).
Figure 5:
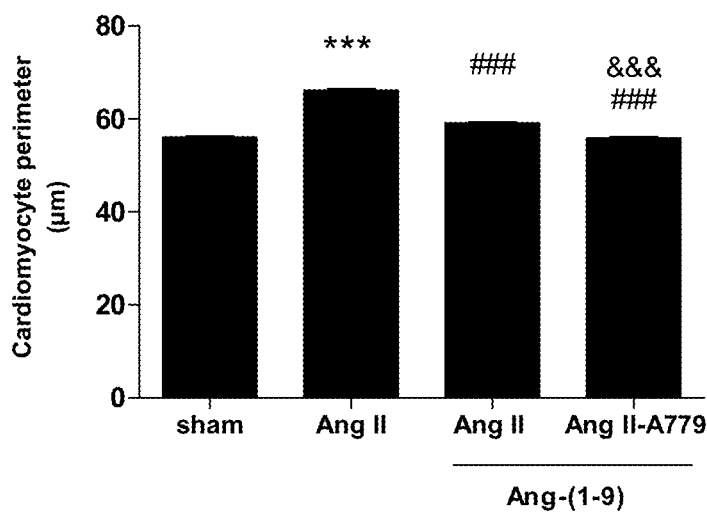

4. Determination of the Cardiomyocyte Hypertrophy Induced by Administration of Angiotensin II The administration of angiotensin II increased the cell area by 37% (204±1 vs. 282±2 µm$^2$, $p<0.001$; FIG. 5A) and the perimeter by 18% (56.1±0.2 vs. 66.2±0.3 µm, $p<0.001$, FIG. 5B), as compared to the Sham control group. The co-administration of angiotensin-(1-9) prevented the increase in size of angiotensin II-induced cardiomyocyte (FIG. 5A), with significant reduction by 20% in the cell area (282±2 vs. 227±2 µm$^2$, $p<0.001$, FIG. 5A) and by 11% in the cell perimeter (66.2±0.3 vs. 59.1±0.3 µm, $p<0.001$, FIG. 5B), as compared to the group infused with angiotensin II alone.

Due to the fact that angiotensin-(1-9) is a precursor of angiotensin-(1-7), the Mas receptor antagonist, A779, was used to rule out the involvement of angiotensin-(1-7) in the effects of angiotensin-(1-9). FIG. 5A shows that A779 did not inhibit the antihypertrophic effect of angiotensin-(1-9), since this peptide also reduced the cell area by 31% (282±1 vs. 195±2 µm$^2$, $p<0.001$, FIG. 5B) and the perimeter by 15.5% (66.2±0.3 vs. 55.9±0.2 µm, $p<0.001$, FIG. 5B) as compared to the group infused with angiotensin II alone. The co-administration of angiotensin-(1-9), A779 together with angiotensin II was more effective in reducing the area (14%, 227±2 vs. 195±2 µm$^2$, $p<0.001$; FIG. 5A) and perimeter (5%, 59.1±0.3 vs. 55.9±0.2 µm, $p<0.001$, FIG. 5B) as compared to the experimental group that received only angiotensin-(1-9) in the presence of angiotensin II.

5. Levels of TGF-β and MCP-1 mRNA

Figure 6:
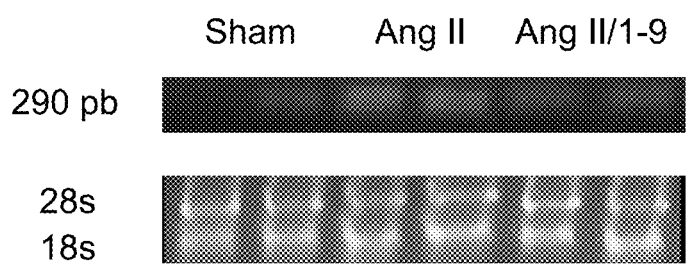
FIG. 6. Effect of the continuous administration of angiotensin-(1-9) on the mRNA levels for TGF-β in the aortic wall of hypertensive rats by angiotensin II infusion. The TGF-β mRNA levels were normalized to the 18S ribosomal RNA band. The values represent the mean±SEM, N=8 #p<0.05 vs. angiotensin II, $*p<0.05$ vs. Sham (after significant ANOVA).
Figure 6:
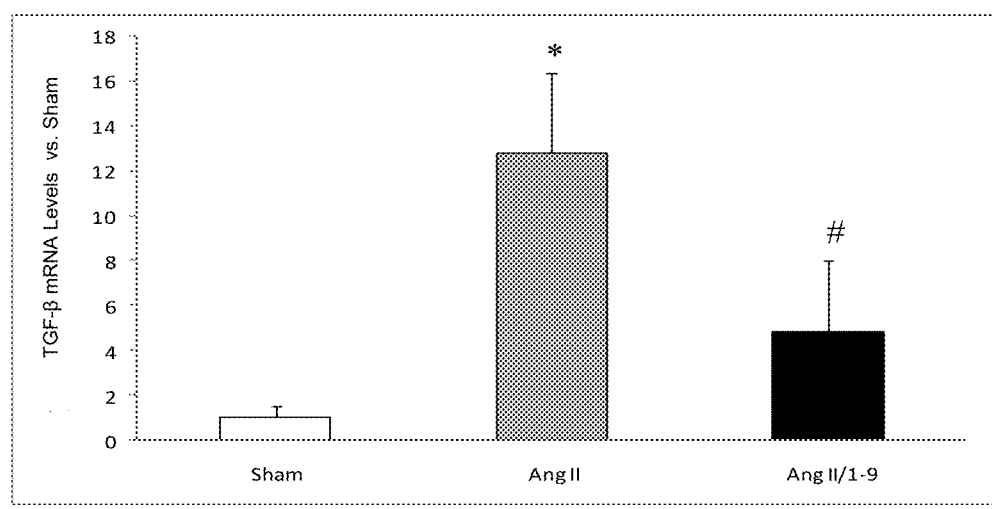
Figure 7:
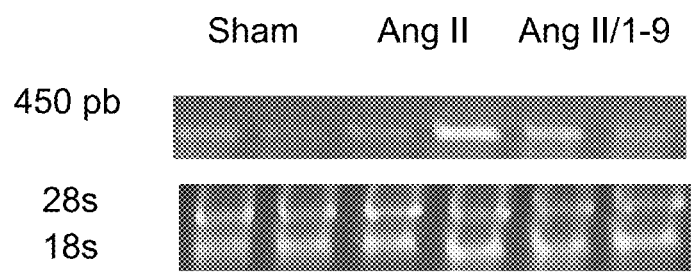
FIG. 7. Effect of the continuous administration of angiotensin-(1-9) on the mRNA levels for MCP-1 in the aortic wall hypertensive rats by angiotensin II infusion. The MCP-1 mRNA levels were normalized to the 18S ribosomal RNA band. The values represent the mean±SEM. N=8
Figure 7:
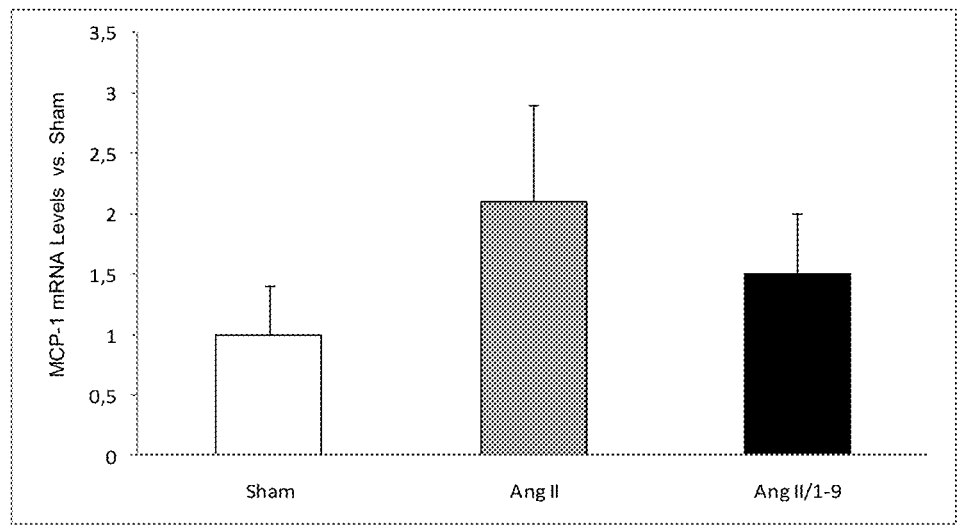

The administration of angiotensin II increased significantly the levels of vascular inflammation determined by increasing TGF-β mRNA in relation to their Sham control (12.8 times) (FIG. 6), with no differences in the MCP-1 mRNA levels (FIG. 6). The administration of angiotensin-(1-9) reduced significantly the TGF-β mRNA levels by 62.5% (FIG. 6), while MCP-1 mRNA showed no differences (FIG. 7).

6. Protein Levels of Collagen I by Western Blot

Figure 8:
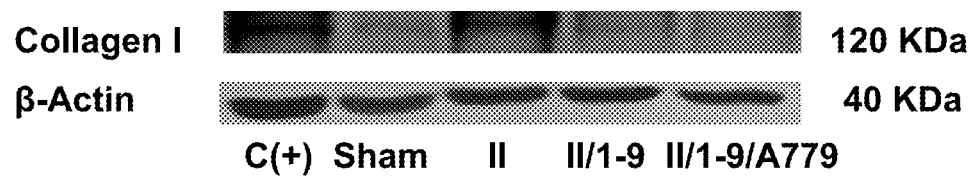
FIG. 8. Effect of the continuous administration of angiotensin-(1-9) on the protein collagen I levels in the aortic wall of hypertensive rats by angiotensin II infusion. The values obtained by Western blot represent the mean±SEM. N=8-12. β-actin was used as a loading control. $^\#p<0.05$ vs. angiotensin II, $*p<0.05$ vs. Sham (after significant ANOVA).
Figure 8:
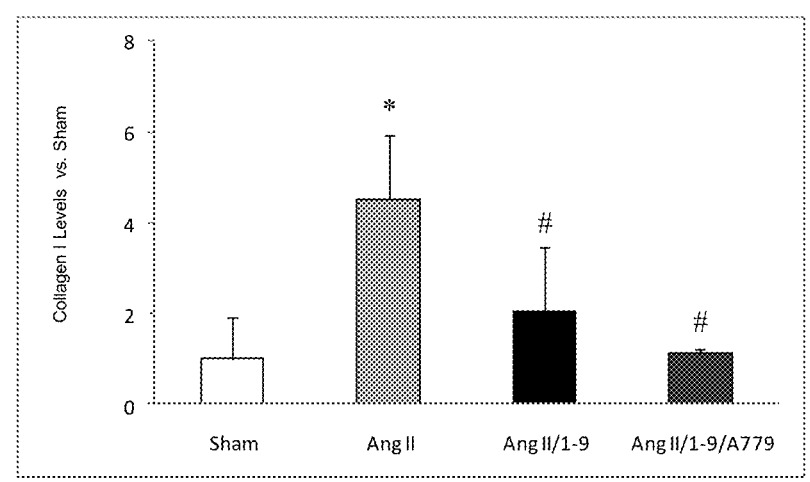

Collagen I was increased significantly in angiotensin II-hypertensive rats as compared to the Sham control group (4.5 times, FIG. 8). The administration of angiotensin-(1-9) prevented by 60% the increase of collagen in the aortic wall, and the co-administration of A779 did not alter the effect of angiotensin-(1-9) (FIG. 8).

In summary, the results shown in this example show that: A) The systolic blood pressure was significantly increased in rats with chronic administration of angiotensin II. B) The administration of angiotensin-(1-9) prevented hypertension and its effect was independent from angiotensin-(1-7). C) Angiotensin-(1-9) prevented the hypertrophy of the aortic wall by angiotensin II. The antihypertrophic effect of angiotensin-(1-9) was direct and independent from angiotensin-(1-7) (it was not inhibited by A779). D) Angiotensin II increased the expression levels of TGF-β and the collagen content in the aortic wall. Angiotensin-(1-9) in the doses used prevented the expression of markers of vascular remodeling and its effect was independent of angiotensin-(1-7). These results clearly show that angiotensin-(1-9) prevents hypertension and remodeling of the aortic wall.

Example 5

Angiotensin-(1-9) Reverts the Increase in Blood Pressure and Cardiovascular Remodeling in the Goldblatt Model (GB, 2 Kidneys, 1 Pinch)

1. Body Weight (BW), Cardiac Mass (CM) and Relative Cardiac Mass (RCM).

Table 2 summarizes the BW, SBP and RCM of Sham, GB and GB+angiotensin-(1-9) rats. No differences in the BW of the three experimental groups evaluated were observed, although the BW in the Gb+angiotensin-(1-9) rats were lower. On the other hand, the BW was elevated significantly in hypertensive animals as compared to control animals (0.93±0.04 vs. 0.74±0.01, $p<0.03$, respectively). Angiotensin-(1-9) decreased significantly the BW in rats with HTN as compared to untreated GB animals (0.84±0.03 vs. 0.93±0.04 g, respectively, Table 2).

The RCM showed a significant increase in GB rats vs. Sham rats (400±1 vs. 330±1, $p<0.04$, respectively). The administration of angiotensin-(1-9) decreased the RCM in hypertensive rats (380±2 vs. 400±1), although this did not translate into statistically significant differences (Table 2).

TABLE 2

Effect of angiotensin-(1-9) on body weight, cardiac mass relative to hypertensive rats by clamping the renal artery (Goldblatt model)

| Parameters | S | GB | GB-Ang-(1-9) | GB-Ang-(1-9)-A779 |
|---|---|---|---|---|
| N | 12 | 8 | 7 | |
| BW (g) | 225 ± 12 | 248 ± 14 | 238 ± 6 | 245 ± 21 |

TABLE 2-continued

Effect of angiotensin-(1-9) on body weight, cardiac mass relative to hypertensive rats by clamping the renal artery (Goldblatt model)

| Parameters | S | GB | GB-Ang-(1-9) | GB-Ang-(1-9)-A779 |
|---|---|---|---|---|
| RCM (mg/g) | 0.68 ± 0.01 | 1.01 ± 0.03 * | 0.84 ± 0.04 *# | 0.83 + 0.10 *# |
| CM (g) | 0.33 ± 0.02 | 0.41 ± 0.01 * | 0.37 ± 0.02 | 0.34 + 0.01 # |

The results represent the mean±SEM. S: Sham; Ang: angiotensin; GB: Goldblatt; BW: body weight; SBP, systolic blood pressure; RCM: relative cardiac mass; CM: cardiac mass. *$p<0.05$ vs. S, #$p<0.05$ vs. GB (after significant ANOVA).

2. Systolic Blood Pressure

Figure 9:
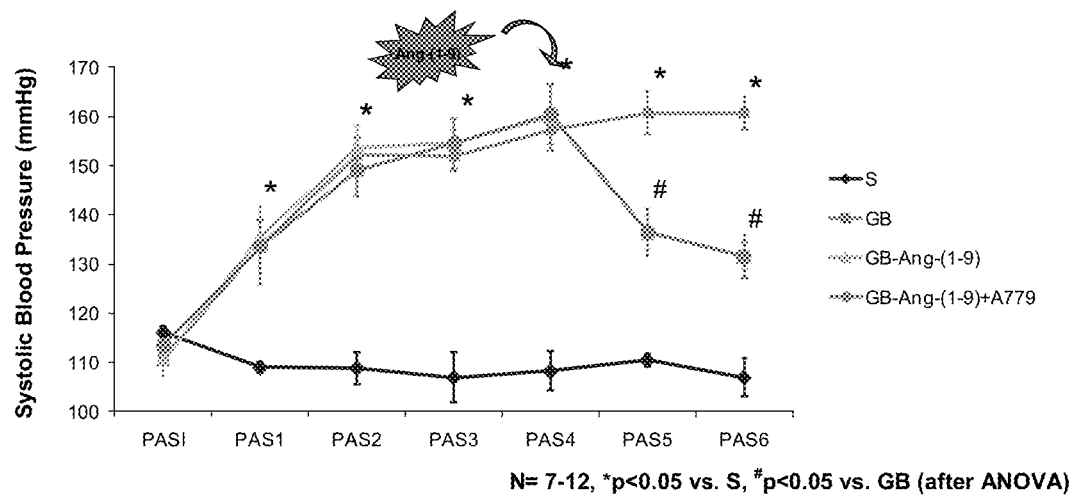
FIG. 9. Effect of the continuous administration of angiotensin-(1-9) on the systolic blood pressure of hypertensive rats by pressure overload, GB model (2 k, 1 clip). The results represent the mean±SEM, with N=7-12. $*p<0.05$ vs. Sham, $^\#p<0.05$ vs. GB (after ANOVA). ♦: normotensive rats, ■: GB hypertensive rats, ▲: treatment of hypertensive rats with angiotensin-(1-9), ●: treatment of hypertensive rats with angiotensin-(1-9) and A779 (angiotensin receptor inhibitor (1-7)).

The Sham rats showed levels of systolic blood pressure in normotensive ranges and close to 110 mmHg between weeks 1 and 6 of the assay (FIG. 9). The GB rats increased significantly their systolic blood pressure from week 1 after surgery, which remained elevated and significantly higher during the 6-week assay. The continuous administration of angiotensin-(1-9) to GB rats from week 4 after surgery decreased by 15% and the systolic blood pressure significantly from week 1 after the administration and it was maintained during the 2-week assay (FIG. 9). The antihypertensive effect of angiotensin-(1-9) was not reversed by the co-administration of the angiotensin-(1-7) receptor inhibitor, A779 (FIG. 9).

3. Morphometric Determination of Hypertensive Myocardial Hypertrophy

Figure 10:
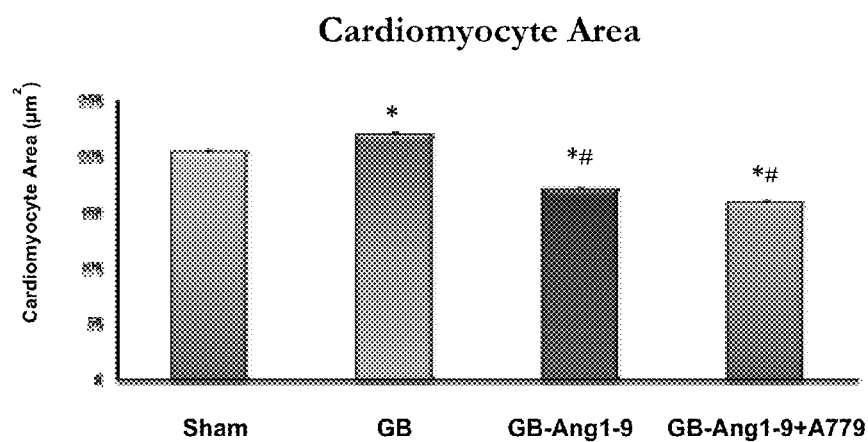
FIG. 10. Effect of the continuous administration of angiotensin-(1-9) on the cardiomyocyte hypertrophy of hypertensive rats by pressure overload. In cross sections of ventricles and stained with hematoxylin-eosin, the area (A) and perimeter (B) of the cardiomyocytes were analyzed. N=7-12. S=Sham rats, GB=Goldblatt hypertensive rats, GB-angiotensin-(1-9)=Goldblatt hypertensive rats with angiotensin-(1-9), $*p<0.05$ vs. S, $^\#p<0.05$ vs. GB (after significant ANOVA).
Figure 10:
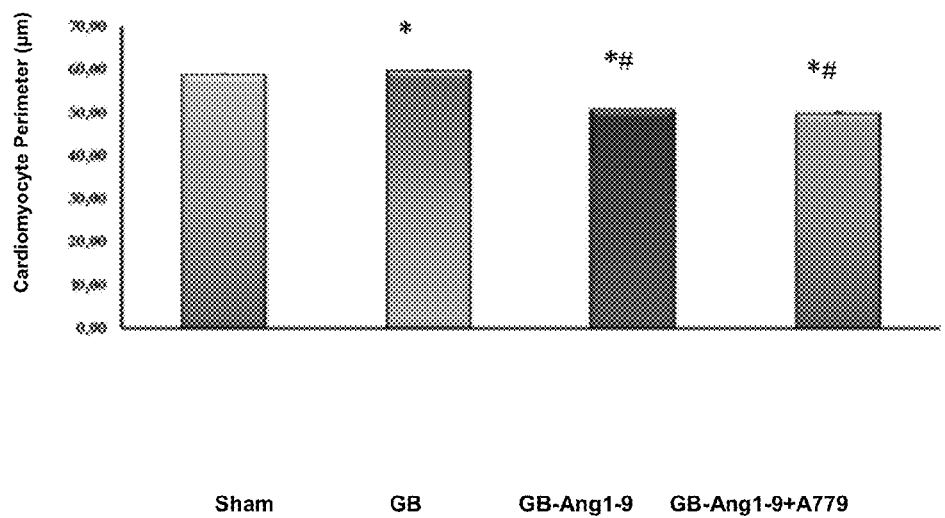
Figure 11:
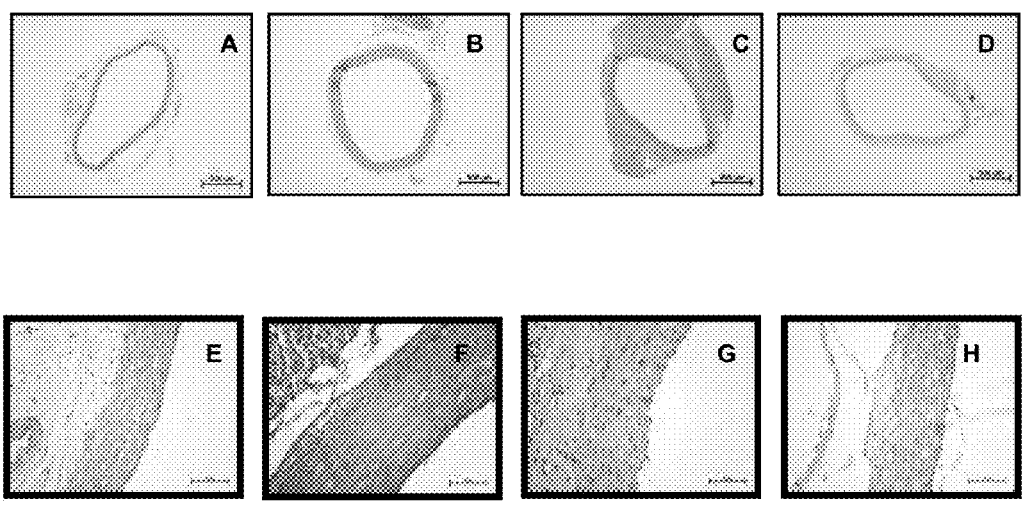
FIG. 11. Effect of angiotensin-(1-9) on the reduction of hypertrophy in the aortic wall of hypertensive rats by pressure overload. Cross sections, panels A, B, C and D (4x) and E, F, G and H (40x) of thoracic aortas of Sham animals (A and E), angiotensin II (B and F), angiotensin II/1-9 (C and G) and angiotensin II/1-9/A779 (D and H). Top bar: 0.5 mm and bottom bar: 50 μm.
Figure 12:
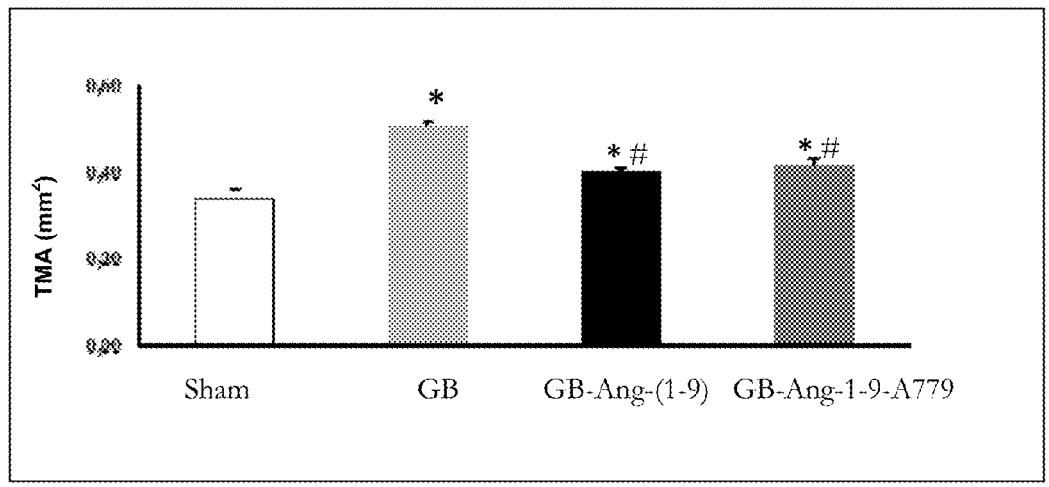
FIG. 12. Effect of the continuous administration of angiotensin-(1-9) on the reduction of the tunica media area (TMA) of thoracic aortas of hypertensive rats by pressure overload. The values represent the mean±SEM. N=9-12. $*p<0.05$ vs. S, $^\#p<0.05$ vs. GB (after significant ANOVA).
Figure 13:
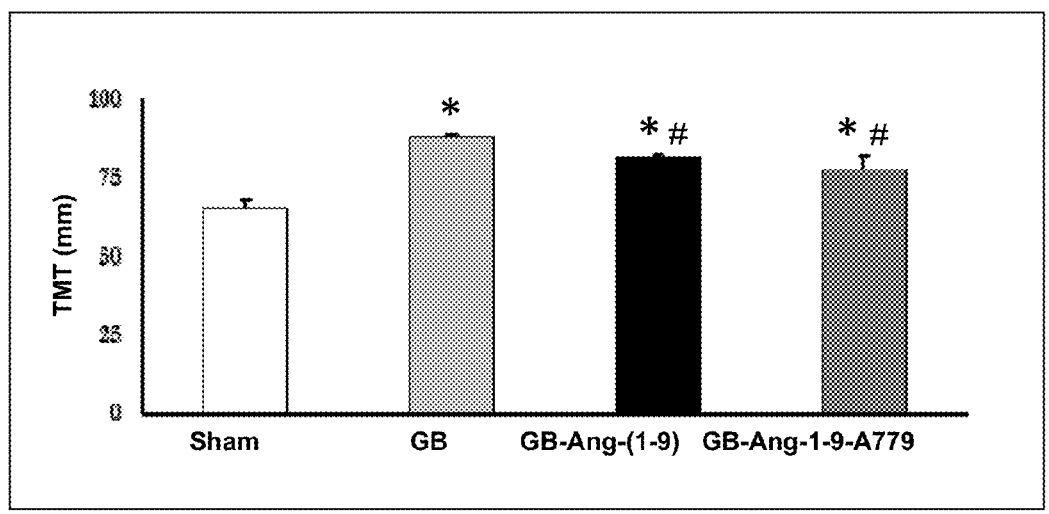
FIG. 13. Effect of the continuous administration of angiotensin-(1-9) on the reduction of the tunica media thickness (TMT) of thoracic aortas of hypertensive rats by pressure overload. The values represent the mean±SEM. N=9-12. $*p<0.05$ vs. S, $^\#p<0.05$ vs. GB (after significant ANOVA).
Figure 14:
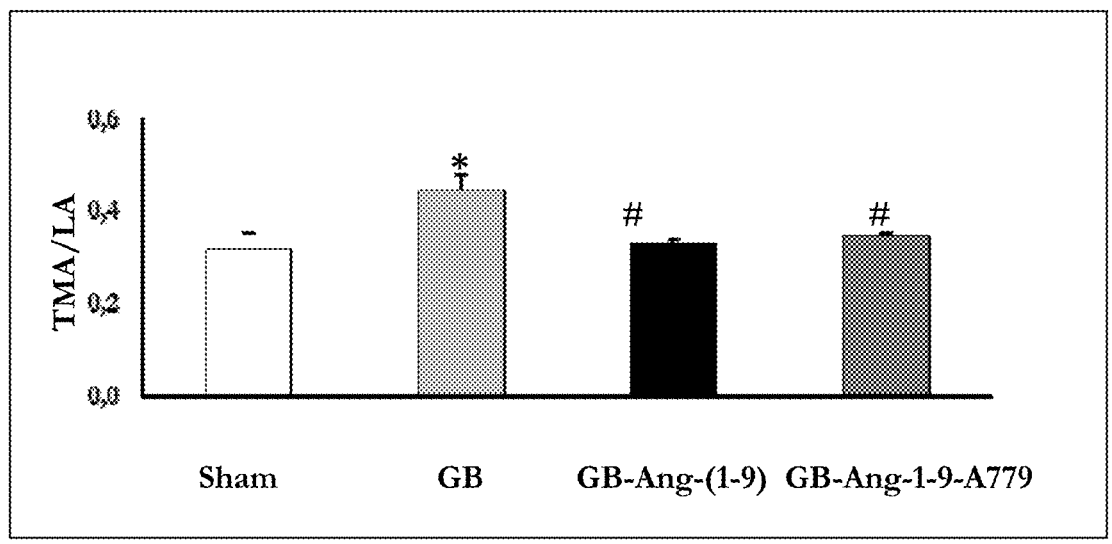
FIG. 14. Effect of the continuous administration of angiotensin-(1-9) on the reduction of the ratio tunica media area to lumen area (TMA/LA) of thoracic aortas of hypertensive rats by pressure overload. The values represent the mean±SEM. N=9-12. $*p<0.05$ vs. S, $^\#p<0.05$ vs. GB (after significant ANOVA).

The evaluation of the cardiomyocyte area and perimeter in hypertensive rats showed significant increases as compared to Sham rats (218±2 vs. 203±2 μm² and 60±1 vs. 55±1 μm, respectively) (FIG. 10). However, the administration of angiotensin-(1-9) decreased the cardiomyocyte area and perimeter by 16% and 22% respectively, as compared to hypertensive rats (FIG. 10). The hypertrophic effect of angiotensin-(1-9) was not reversed by the co-administration of the angiotensin-(1-7) receptor inhibitor, A779 (FIG. 10).

4. Vascular Hypertrophy

Figure 15:
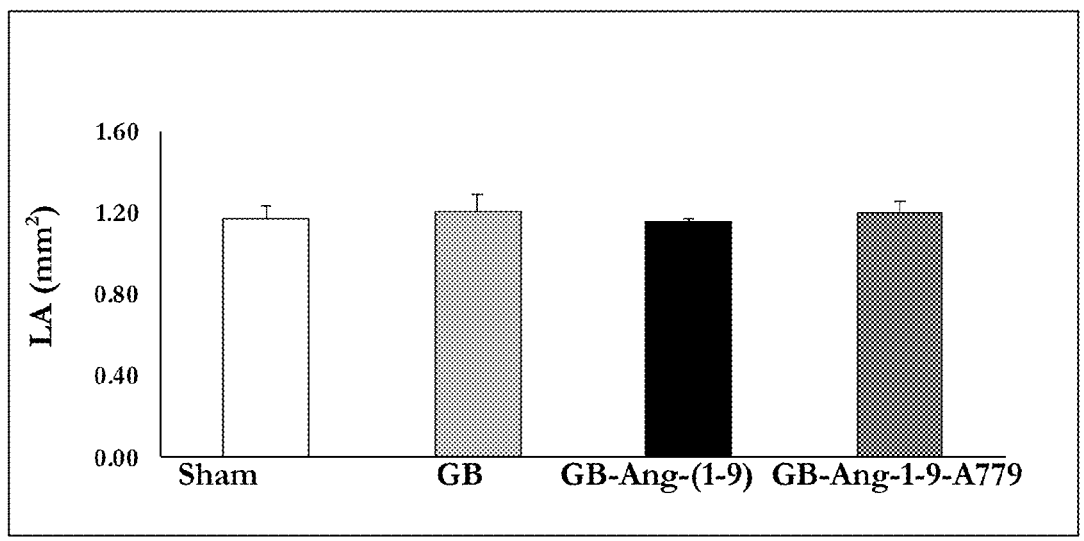
FIG. 15. Effect of the continuous administration of angiotensin-(1-9) on the lumen area (LA) of thoracic aortas of hypertensive rats by pressure overload. The values represent the mean±SEM. N=9-12.
Figure 16:
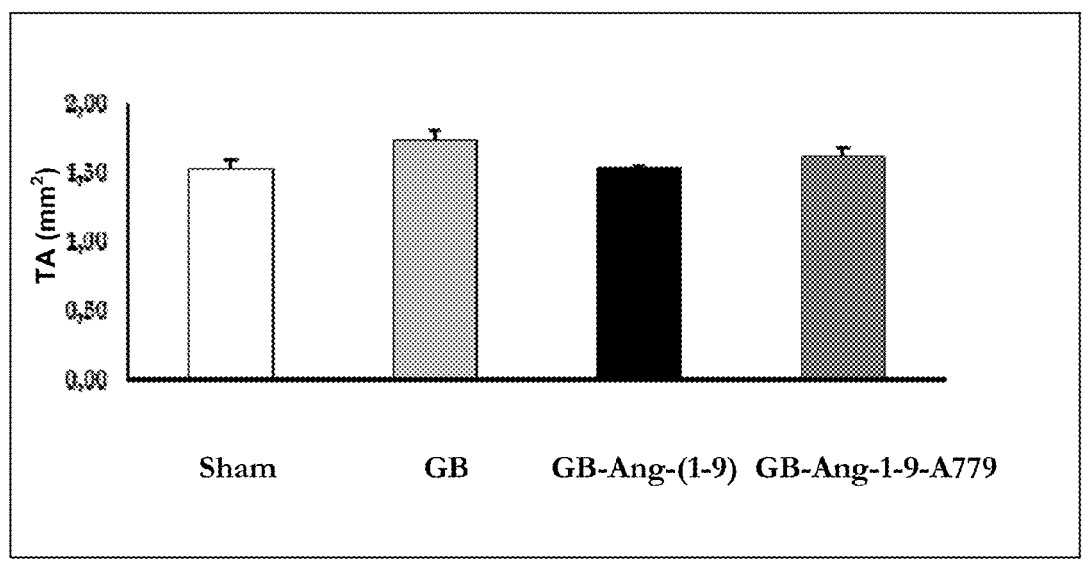
FIG. 16. Effect of the continuous administration of angiotensin-(1-9) on the total area of thoracic aortas of hypertensive rats by pressure overload. The values represent the mean±SEM. N=9-12.

Hypertension induced by clamping the renal artery increased significantly the tunica media area (TMA), tunica media thickness (TMT) and the ratio of TMA to lumen area (LA) (FIGS. 11-14) as compared to the control group, without changes in the LA (FIG. 15) and the total area (FIG. 16). Confusion with angiotensin-(1-9) reduced significantly the increase in TMA, TMT and TMA/AL (FIGS. 11-14). The effect of angiotensin-(1-9) was not affected by the administration of A779 (FIGS. 11-14).

5. Protein Levels of Collagen I in the Aortic Wall

Figure 17:
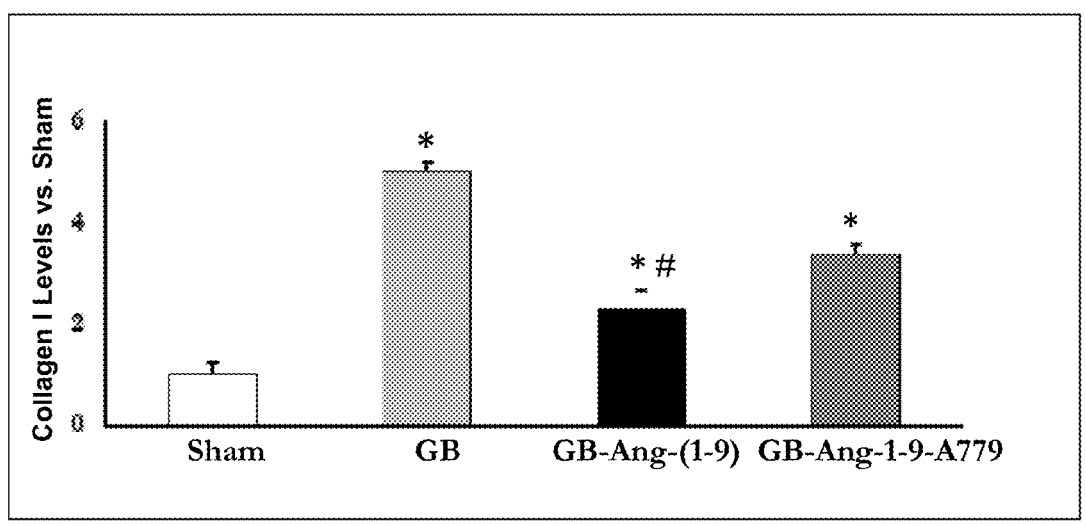
FIG. 17. Effect of the continuous administration of angiotensin-(1-9) on the collagen I protein levels in the aortic wall of hypertensive rats by pressure overload. The values obtained by Western blot represent the mean±SEM. N=3-12. Symbols: #p<0.05 vs. GB, $*p<0.05$ vs. Sham (after significant ANOVA).

Collagen I was increased significantly in hypertensive rats as compared to the Sham control group (5 times, FIG. 17). The administration of angiotensin-(1-9) reduced by 54% the increase of collagen in the aorta wall and the co-administration of A779 did not alter the effect of angiotensin-(1-9) (FIG. 17).

6. Total Collagen Ventricular Content

Figure 18:
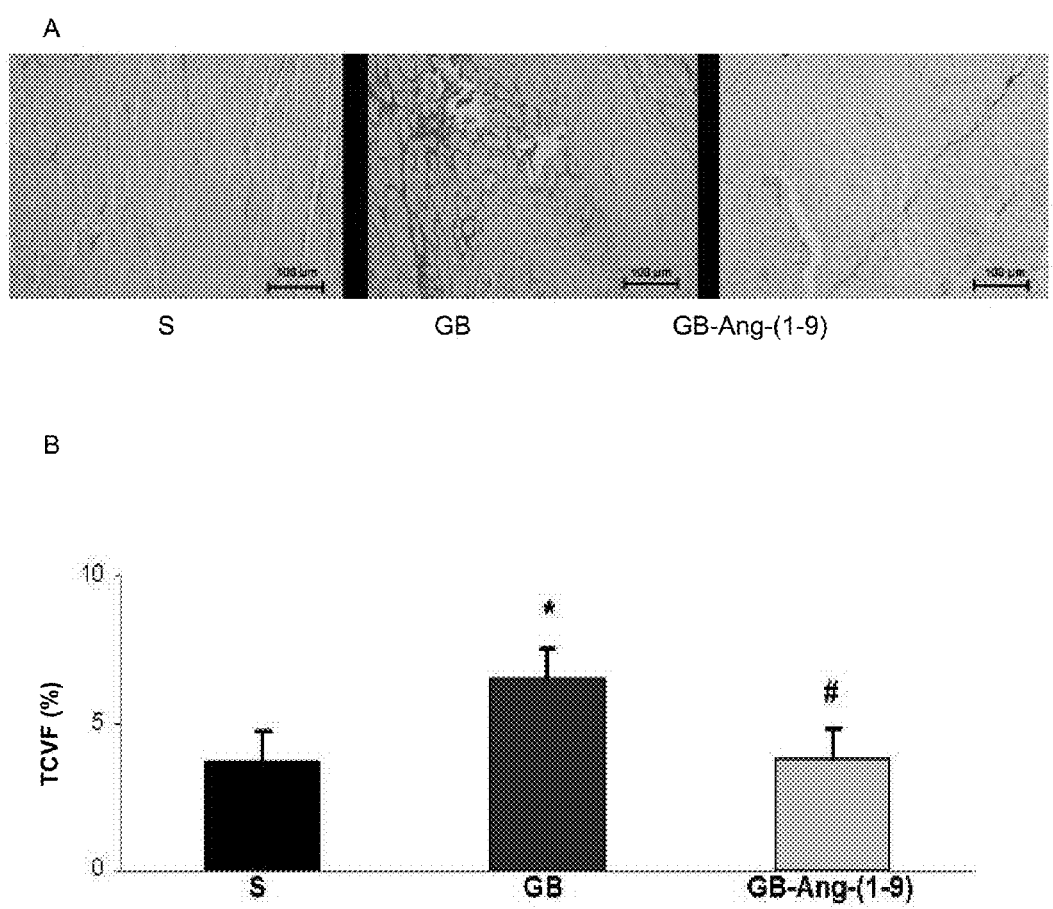
FIG. 18. Effect of the continuous administration of angiotensin-(1-9) on hypertensive myocardial fibrosis by pressure overload. In cross sections of the ventricle stained with picrosirius red (3A), the volume fraction of total collagen (VFTC) was determined. N=7-12. Bar=100 μm. Abbreviations: S=Sham rats, GB=Goldblatt rats, GB-angiotensin-(1-9)=Goldblatt hypertensive rats with angiotensin-(1-9), *p<0.05 vs. S, #p<0.05 vs. GB (after significant ANOVA).

The volume fraction of total collagen (VFTC) showed to be significantly higher in GB rats as compared to Sham rats (6.5±1 and 3.7±1 □□, respectively, FIG. 18). When treating GB rats with angiotensin-(1-9), a significant decrease of VFTC by 41% was observed as compared to untreated hypertensive rats (3.8 vs. 6.5±1 □□, respectively). The VFTC of the GB rats+angiotensin-(1-9) reached values similar to normotensive rats (FIG. 18).

7. TGFβ-1 and ED-1 Levels in the Aortic Wall and Left Ventricular

Figure 19:
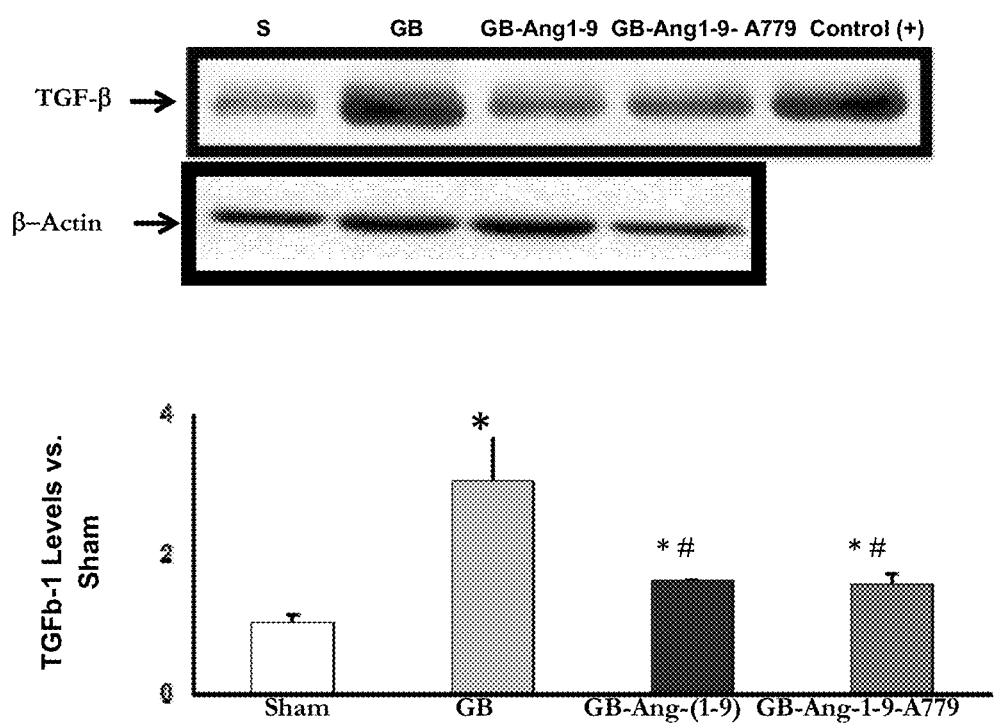
FIG. 19. Effect of the continuous administration of angiotensin-(1-9) on the TGFβ-1 protein levels in the aortic wall of hypertensive rats by pressure overload. The values obtained by Western blot represent the mean±SEM. N=8-12. β-actin was used as a loading control. #p<0.05 vs. angiotensin II, *p<0.05 vs. Sham (after significant ANOVA).
Figure 20:
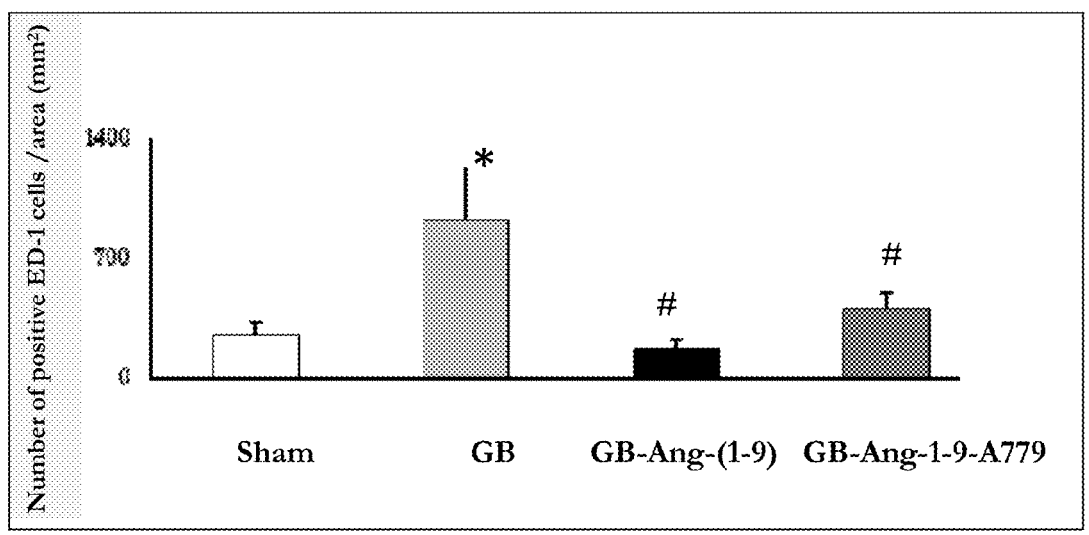
FIG. 20. Effect of angiotensin-(1-9) on the levels of ED-1 of the aortic wall of hypertensive rats by pressure overload. Cross sections of the thoracic aorta were immunostained with anti-ED-1. *p<0.05 vs. S, #p<0.05 vs. GB (after significant ANOVA).

Hypertension increased significantly the vascular inflammation determined by increasing the TGFβ-1 and ED-1 levels as compared to the Sham control (3.0 and 3.7 times, respectively, FIGS. 19 and 20). The administration of angiotensin-(1-9) decreased significantly the TGFβ-1 and ED-1 levels by 47% and 82%, respectively (FIGS. 19 and 20), while A779 did not alter the effect of angiotensin-(1-9) (FIGS. 19 and 20).

At the level of the left ventricle, the ED-1 levels showed a significant increase in GB rats vs. Sham animals (Table 3). The administration of angiotensin-(1-9) decreased significantly ED-1 in the ventricles of the hypertensive rats. The antagonist A779 did not alter the effect of angiotensin-(1-9) (Table 3).

TABLE 3

Effect of angiotensin-(1-9) on the ventricular content of ED-1

| Experimental Group | N | Assigned value | # Positive cells | Meaning |
|---|---|---|---|---|
| S | 7 | 0 | 0 | Without presence of ED-1 |
| GB | 7 | 2* | 20-40 | Moderated number of ED-1 homogeneously distributed |
| GB- angiotensina-(1-9) | 7 | 1# | 0-20 | Low number of ED1 and isolated |
| GB-angiotensina-(1-9)-A779 | 4 | 1# | 0-20 | Low number of ED1 and isolated |

The results represent the mean±SEM. BW: Body weight, SBP: systolic blood pressure, RCM: relative cardiac mass, CM: cardiac mass. *$p<0.05$ vs. S, #$p<0.05$ vs. GB (after ANOVA), *$p<0.05$ vs. S, #$p<0.05$ vs. GB (after significant ANOVA).

Example 6

Determining the Vasoactive Effect of Angiotensin-(1-9)

Contractility Studies in Mesenteric Arteries

The change in diameter of rat resistance (mesenteric) arteries was determined, they were then perfused and pressurized under physiological conditions, in response to different substances, according to a methodology previously described (Gonzalez et al. Hypertension 45:853-9, 2005). Briefly, male rats (Sprague Dawley, 150-200 g) were euthanized for dissection of mesenteric vascular territory, avoiding direct manipulation of arterial or venous tissue. Mesenteric small arteries (200-300 micrometers) were isolated, surgically eliminating adventitial tissue under a zoom stereo microscope (Olympus SZ61). The arteries were perfused intraluminally into a thermoregulated bath at controlled pressure and flow, with perfusion solution (modified Krebs, KRB) of the following composition, in mmol/L: NaCl, 130; $CaCl_2$, 2.5; $NaHCO_3$, 25; $MgSO_4$, 1.2; $NaH_2PO_4$, 1.2; KCl, 4.7; glucose, 5.5, pH 7.4. Before use, KRB was gassed with a mixture of 95% $O_2$ and 5% $CO_2$. For perfusion, the artery was cannulated with a glass micropipette (outer diameter 164μ), secured with 5-0 silk suture. The arteries were perfused with 10-20 μL/min KRB, so as to achieve transmural pressure of 60 mmHg. After a rest period of 20 minutes, each artery was incubated in the presence of a vasoconstrictor (100 μM phenylephrine) for two minutes and an endothelial NO production agonist (1 μM acetylcholine). These stimuli allowed proving the feasibility of the tunica media and the endothelium. In the cases where appropriate responses were observed, the artery was washed and, after a new equilibration period, it was used to test the direct vasoconstrictor effects of angiotensin-(1-9) or vasodilatory effects after pre-contraction with phenylephrine. To assess the involvement of endothelial factors in the potential vasoactive effect of angiotensin-(1-9), in some experiments the endothelium was removed by mechanical abrasion.

Example 7

Effect of Angiotensin-(1-9) on Vasodilation

Figure 21:
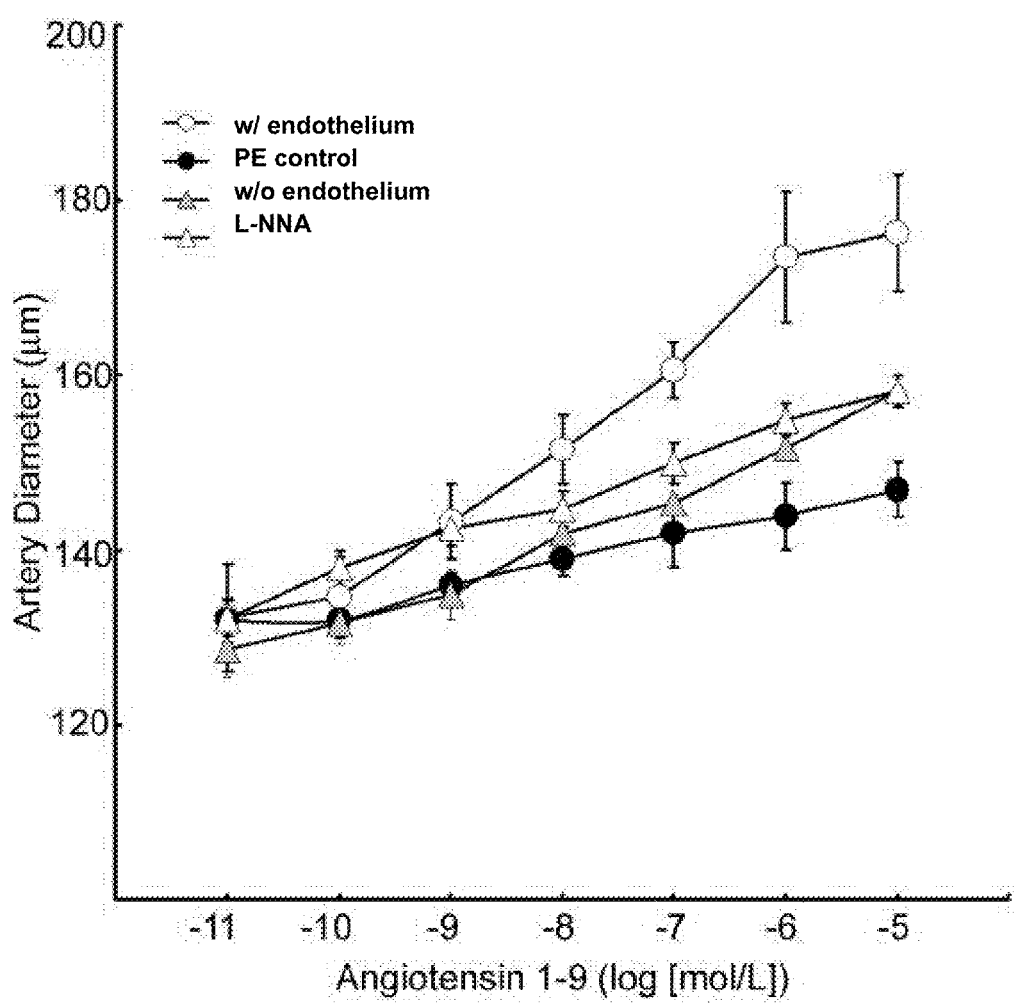
FIG. 21. Effect of angiotensin-(1-9) on the vasodilation of rat mesenteric arteries. It was determined the diameter of control arteries with endothelium (○), treated with phenylephrine (●, vasoconstriction control), without endothelium (▲) and treated with L-NNA (Δ, inhibitor of nitric oxide synthase), in the presence of different doses of angiotensin-(1-9).

Angiotensin-(1-9) increased in a dose-dependent manner the diameter of resistance arteries with intact endothelium as compared to arteries the endothelium was removed therefrom (FIG. 21). As a positive control of the assay, arteries stimulated with a known vasoconstrictor agent such as phenylephrine were used. In order to determine the vasodilator mechanism of angiotensin-(1-9), the mesenteric arteries with angiotensin-(1-9) were co-incubated together with a nitric oxide synthase inhibitor (L-NAME). It was observed that L-NAME decreased the vasodilator effect of angiotensin-(1-9); hence, the mechanism of the vasodilatory action of angiotensin-(1-9) is dependent on nitric oxide (FIG. 21).

Example 8

Preparation of Viral Vectors Overexpressing the Homologous Angiotensin-1 Converting Enzyme (ACE-2)

1. Preparation of an Adenovirus Overexpressing the Homologous Angiotensin-1 Converting Enzyme.

Figure 22:
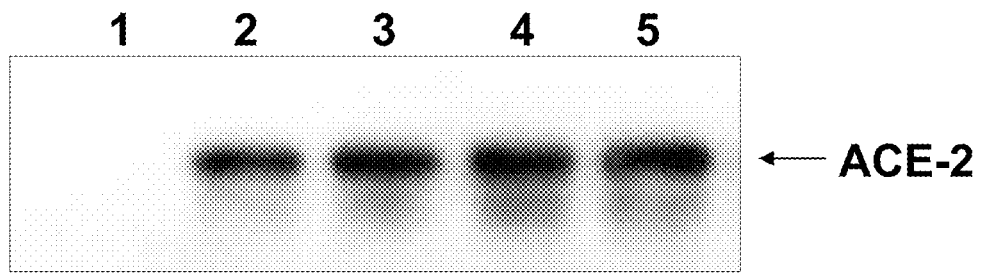
FIG. 22. ACE2 overexpression by adenoviral transduction in cardiomyocytes in culture. Cardiomyocytes in culture were transduced with an ACE-2-overexpressing adenovirus using different multiplicities of infection (MOI). The MOIs used were: lane 1: MOI=0, lane 2: MOI=1000, lane 3: MOI=2000, lane 4: MOI=3000, lane 5: MOI=4000. After 48 h incubation at 37 in an incubator with 5% CO2/95% air, the cells were lysed and subjected to polyacrylamide gel electrophoresis in the presence of SDS and subsequent western blot, using a polyclonal anti-ACE2 antibody.

Initially, the ACE2 gene (human, Genebank accession code: NM_021804; rat, Genebank accession code: NM_001012006) was subcloned into the adenoviral plasmid pDC316 (Microbix Byosystem Inc.). The positive clones were confirmed by sequencing. Thereafter, the plasmid pDC316 containing the gene for ACE2 was co-transfected with the adenoviral plasmid pBHGlox(delta)E1,3Cre into HEK293 cells. The recombinant adenovirus was obtained by homologous recombination between the two plasmids according to the method described by Hardy et al. (J. Virol. 71:1842-9, 1997). The confirmation that the resulting adenovirus overexpressed ACE2 was carried out via transduction of neonatal rat cardiomyocytes in a culture with different multiplicities of infection (MOI) with the adenovirus expressing ACE2. The overexpression of ACE2 was verified by measuring the ACE2 protein levels by Western blot and by enzymatic activity of ACE2. FIG. 22 shows the overexpression of ACE2 in a cardiomyocyte culture using different multiplicities of infection (MOI) with an ACE-2-overexpressing adenovirus. Normally, it is not possible to detect the presence of ACE-2 in a cardiomyocyte culture, but through the expression of ACE-2 using an adenovirus it is possible to raise by several hundred times the levels of ACE-2 (FIG. 22).

2. Preparation of a Lentivirus Overexpressing the Homologous Angiotensin-I Converting Enzyme.

Initially, the ACE2 gene (human, Genebank accession code: NM_021804; rat, Genebank accession code: NM_001012006) was subcloned into the lentiviral plasmid PHAGE-PGK. Lentiviruses were produced in HEK293T cells by simultaneously co-transfecting the lentiviral vector containing the cDNA for ACE2 and the vectors pCMVdeltaR8.9 and pHCMV-G according to the method described by Zufferey et al. (J. Virol. 72:9873-80, 1998). The confirmation that the resulting lentivirus overexpressed ACE2 was carried out via transduction of neonatal rat cardiomyocytes in a culture with different multiplicities of infection (MOI) with the ACE2-expressing lentivirus. The overexpression of ACE2 was verified by measuring the ACE2 protein levels by Western blot and by enzymatic activity of ACE2.

3. Preparation of a Retrovirus Overexpressing the Homologous Angiotensin I Converting Enzyme.

Initially, the ACE2 gene (human, Genebank accession code: NM_021804; rat, Genebank accession code: NM_001012006) was subcloned into the retroviral plasmid PCnBgSN (or any other retroviral plasmid). Retroviruses were produced in HEK293T cells by simultaneously co-transfecting the retroviral vector containing the cDNA for ACE2 and the vectors pHIT60 (for gal-pol) and pCVG (for VSV-G) according to the method described by Yu & Kwon (Methods in Molecular Biology vol. 433: Volume 1: Production and In Vivo Applications, Edited by: J. M. Le Doux© Humana Press, Totowa, N.J., pp 1-16). The confirmation that the resulting retrovirus overexpressed ACE2 was carried out via transduction of neonatal rat cardiomyocytes in culture with different multiplicities of infection (MOI) with the ACE2-expressing retrovirus. The overexpression of ACE2 was verified by measuring the ACE2 protein levels by Western blot and by enzymatic activity of ACE2.

4. Preparation of an Adeno-Associated Virus Overexpressing the Homologous Angiotensin-I Converting Enzyme.

Initially, the ACE2 gene (human, Genebank accession code: NM_021804; rat, Genebank accession code: NM_001012006) was subcloned into the plasmid of the adeno-associated virus pAAV-MCS (Stratagene). Adeno-associated viruses were produced in HEK293T cells by simultaneously co-transfecting the adeno-associated virus vector containing the cDNA for ACE2 and pAAV-RC (pAAV-helper or pRC, which contains the rep and cap genes) and PAdV-Helper (or pHelper vectors, carrying the E2A, E4 genes and VA-RNAs) according to the method described by Stratagene. The confirmation that the resulting adeno-associated virus overexpressed ACE2 was carried out via transduction of neonatal rat cardiomyocytes in culture with different multiplicities of infection (MOI) with the ACE2-expressing adeno-associated virus. The overexpression of ACE2 was verified by measuring the ACE2 protein levels by Western blot and by enzymatic activity of ACE2.

Example 9

Intracardiac Administration and Administration in Blood Vessels of Viral Vectors Overexpressing the Homologous Angiotensin-I Converting Enzyme (ACE-2)

The animals were infected according to the method described by Coleman et al. (Physiol. Genomics 12:221-8, 2003). Briefly, normotensive male rats of 150□10 g were randomized into GB groups, and as controls pseudo-operated rats (Sham) were used. Five weeks after surgery, the rats with >140 mmHg hypertension were randomized into intra-myocardial infection, as described by Hajjar et al. (Circ. Res. 86:616-621, 2000), with an adenoviral vector overexpressing either ACE2 (AdACE2) or the green fluorescent protein (GFP). The rats were intraperitoneally anesthetized with ketamine and xylazine at doses of 50 mg/Kg/weight and 10 mg/Kg/weight, respectively; they were subjected to laryngeal cannulation with a 18-gauge soft catheter, and then ventilated with a tidal volume of approximately 2 mL at 60 cycles/min (mechanical ventilator SAR-830 for small animals). A thoracotomy at the fifth left intercostal space was conducted, wherein a 24-gauge catheter with 30 µL solution of sterile adenoviral, lentiviral or adeno-associated virus was introduced into the left ventricular chamber. After installing a drainage tube for removal of air and blood, the incision was closed, and then the animals were allowed to recover and were returned to their respective cages. The mortality of this surgery was around 20% and it has been established for long-term gene transfer into myocardial tissue (for details see Methods in Molecular Biology, vol. 219: Cardiac Cell and Gene Transfer, Edited by: J M Metzger© Humana Press Inc., Totowa, N.J.). A week after infection, the rats were euthanized.

Example 10

The Overexpression of ACE-2 Reduces Hypertension and Hypertensive Ventricular Remodeling 1. Body weight (BW), cardiac mass (CM) and relative cardiac mass (RCM).

The BW in AdACE2 rats was significantly lower (−21%) as compared to GB and Sham rats. No BW differences between AdACE2 and AdGFP rats were observed (Table 4).

The CM in GB rats was significantly higher compared to the control group (943±20 vs. 740±20) as well as the RCM (387±16 vs. 334±13). Myocardial infection with AdACE2 or AdGFP did not alter the RCM as compared to GB rats (Table 4). On the other hand, the CM was significantly lower in AdACE2 and AdGFP rats (Table 4).

TABLE 4

Effect of intramyocardial AdACE2 infection on body weight, and cardiac mass in relation to hypertensive rats by pressure overload

| Parameters | S | GB | GB-AdACE2 | GB-AdGFP |
|---|---|---|---|---|
| N | 8 | 8 | 8 | 5 |
| BW (g) | 257 ± 7 | 245 ± 10 | 193 ± 7*# | 211 ± 11* |
| RCM (mg/g) | 330 ± 13 | 387 ± 16* | 495 ± 19# | 476 ± 73# |
| CM (g) | 0.740 ± 0.02 | 0.943 ± 0.02* | 0.812 ± 0.02# | 0.980 ± 0.01*† |

The results represent the mean±SEM. BW: Body weight, RCM: relative cardiac mass, CM: cardiac mass. *$p<0.05$ vs. S, #$p<0.05$ vs. GB, †$p<0.05$ vs. GB-AdECA2 (after significant ANOVA).

2. Systolic Blood Pressure

Sham rats showed levels of systolic blood pressure in normotensive ranges and close to 110 mmHg between weeks 1 and 6 of the assay (Table 5). GB rats increased significantly (42%) systolic blood pressure from week 1 after surgery, which remained elevated and significantly higher during the 6-week assay. The intramyocardial infection of GB rats with AdECA2 from week 5 after surgery decreased significantly by 15%, blood pressure after one week of administration (Table 5). The GB-AdGFP group also showed a significant decrease in SBP (−22%, Table 5).

TABLE 5

Effect of intramyocardial AdACE2 infection on systolic blood pressure of hypertensive rats by pressure overload

| SBP (mmHg) | S | GB | GB-AdACE2 | GB-AcGFP |
|---|---|---|---|---|
| N | 8 | 8 | 8 | 5 |
| Initial SBP | 113 ± 3 | 110 ± 2 | 110 ± 4 | 113 ± 4 |
| SBP week 1 | 114 ± 3 | 133 ± 6* | 125 ± 7*# | 142 ± 6* |
| SBP week 5 | 110 ± 3 | 157 ± 4* | 175 ± 7*# | 163 ± 7* |
| SBP week 6 | 110 ± 3 | 156 ± 3* | 133 ± 9*# | 122 ± 5# |

The results represent the mean±SEM. SBP: systolic blood pressure. *$p<0.05$ vs. S, #$p<0.05$ vs. GB (after significant ANOVA).

3. Hypertensive Cardiomyocyte Hypertrophy

Figure 23:
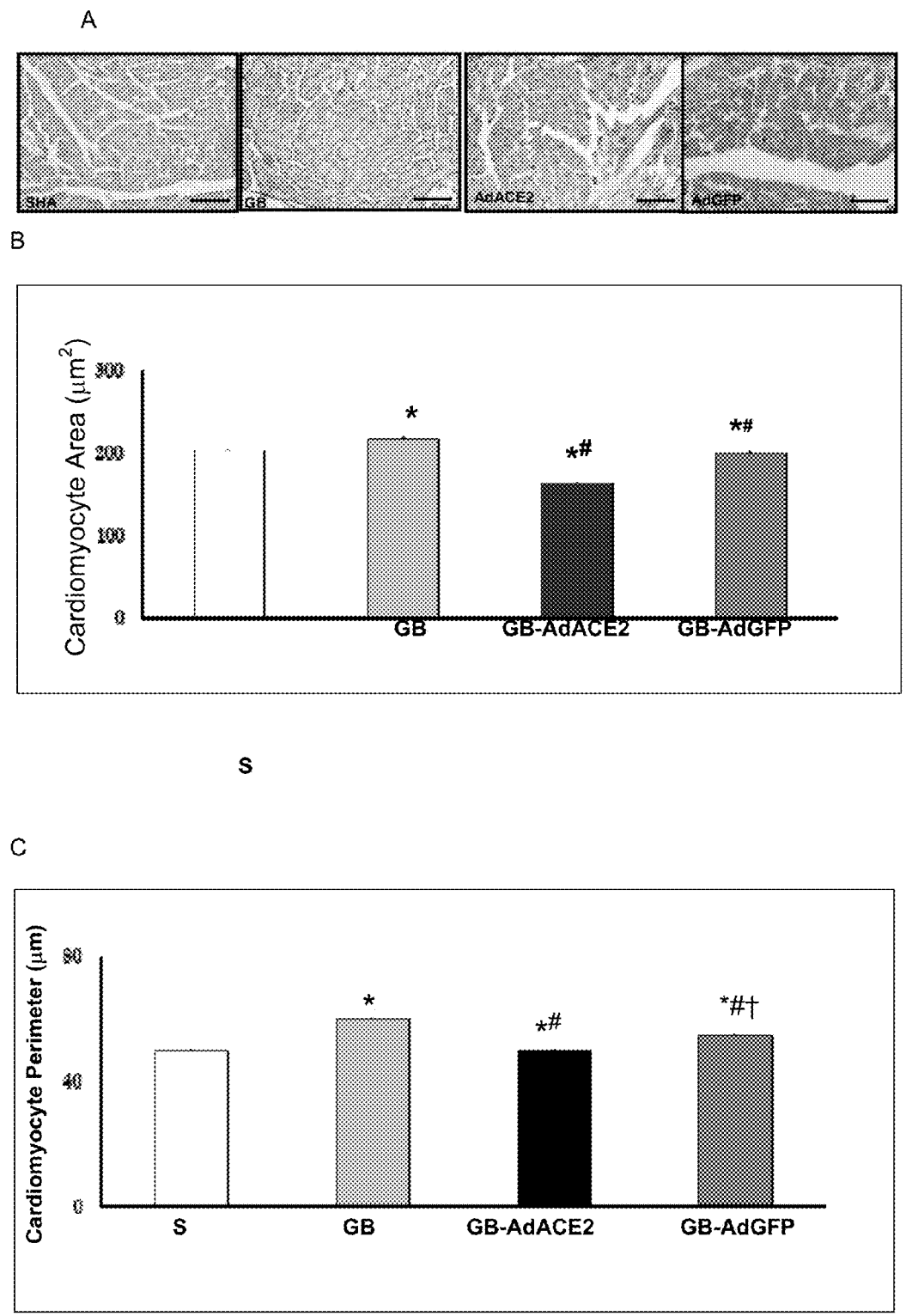
FIG. 23. Effect of ACE2 over-expression on hypertensive cardiac hypertrophy induced by pressure overload. After one week of infection with the adenoviral vector, the ventricle was removed, treated, cut and measured as described in the section Materials and Method. A) Representative image of cardiomyocytes from Sham rats, Goldblatt rats (GB), Goldblatt rats treated with AdACE2 (GB-AdACE2), and Goldblatt rats treated with AdGFP (GB-AdGFP). The bar equals 50 μm. Photos taken at 40×. B) Quantification of the cardiomyocyte area. C) Evaluation of the cardiomyocyte perimeter. The values represent the mean±SEM, N=5-8. *p<0.05 vs. S, #p<0.05 vs. GB, † p<0.05 vs. GB-AdACE2.

Hypertension increased significantly the cardiomyocyte area in relation to their Sham controls (217±2 vs. 203±1, respectively, FIG. 23A). Myocardial AdACE2 infection reduced significantly the cardiomyocyte area as compared to the GB group (−25%, respectively, FIG. 23B). The experimental group corresponding to the GFP infection control showed no differences in the cardiomyocyte area as compared to hypertensive rats (FIGS. 23A and B).

The cardiomyocyte perimeter of hypertensive rats was significantly higher as compared to their Sham controls (20%, FIG. 23C). The overexpression of ACE2 in hypertensive rats decreased significantly the cardiomyocyte perimeter relative to the one observed in GB rats (−17%, FIG. 23C). Although the perimeter of rats infected with GFP was shown to be lower than that of GB rats (−8%), this effect was less than that the one observed with AdACE2.

4. Hypertensive Cardiac Fibrosis

Figure 24:
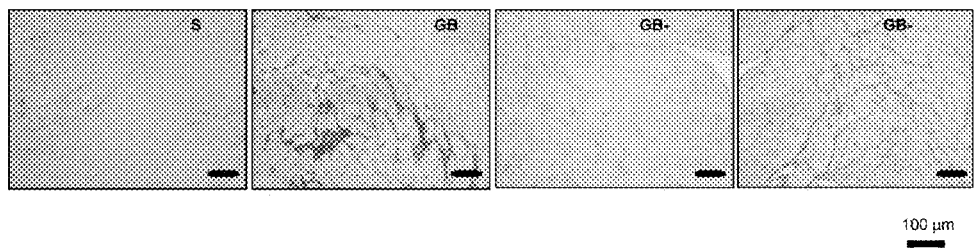
FIG. 24. Effect of ACE2 overexpression on the volume fraction of total collagen in the ventricle. A) Representative image of cross sections of the ventricle stained with picrosirius red. Bar=100 um. Abbreviations: S=Sham rats, GB=Goldblatt rats, GB-AdECA2)=Goldblatt hypertensive rats infected with AdECA2 angiotensin-(1-9), GB-AdGFP=Goldblatt hypertensive rats infected with AdGFP. Photos taken at 40×. B) Quantification of the volume fraction of collagen. Values are presented as mean±SEM, N=7-12. *p<0.05 vs S, # p<0.05 vs GB (post significant ANOVA).
Figure 24:
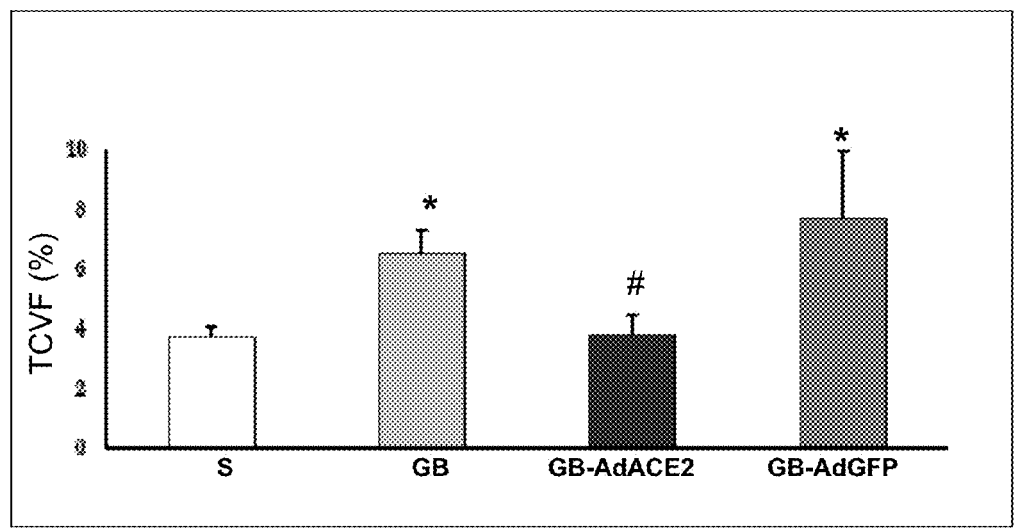

The total collagen content was significantly higher in hypertensive rats as compared to the Sham control group (6.5±0.8 vs. 3.7±0.4, respectively, FIG. 24). Intramyocardial AdACE2 infection reduced significantly the collagen content in relation to hypertensive rats (3.6±1.7 vs. 6.5±2.4, respectively, FIG. 24). The collagen content in rats infected with AdGFP was similar to that obtained in GB rats (FIG. 24).

The invention claimed is:

1. A method of treating hypertension, which comprises administering an effective amount to a patient in need thereof angiotensin-(1-9) peptide.

2. A method of inducing vasodilation, which comprises administering an effective amount to a patient in need thereof angiotensin-(1-9).

3. The method according to claim 1, further comprising preventing, reverting, inhibiting and/or reducing cardiovascular, renal, pulmonary, cerebral damage caused by hypertension.

4. The method according to claim 1, wherein said angiotensin-(1-9) peptide is in a pharmaceutical injectable form.

5. The method according to claim 1, wherein the angiotensin-(1-9) peptide is administered in a form that is released continuously inside the body.

6. The method according to claim 1 wherein the angiotensin-(1-9) peptide is administered with a continuous release pump.

7. The method according to claim 5, wherein said continuous release is carried out via intravenous, intramuscular, intradermal, subcutaneous, or intraperitoneal route.

8. The method according to claim 1, wherein said angiotensin-(1-9) peptide is in oral or rectal pharmaceutical form.

9. The method according to claim 1, which comprises overexpressing the homologous angiotensin-I converting enzyme (ACE2).

10. The method according to claim 9, wherein the overexpression of the homologous angiotensin-I converting enzyme (ACE2) is obtained by adenovirus, adeno-associated virus, retrovirus, lentivirus.

11. A method of treating hypertension, which comprises administering to a patient in need thereof angiotensin-(1-9) peptide and at least one pharmaceutical compound selected from angiotensin-I converting enzyme inhibitors, angiotensin-II receptor antagonists (ARA II), Rho kinase inhibitors, renin inhibitors, L-type calcium channel antagonists and diuretics.

12. The method according to claim 2, wherein said wherein said angiotensin-(1-9) is in a pharmaceutical injectable form.

13. The method according to claim 2, wherein the angiotensin-(1-9) peptide or derivatives of said peptide is administered in a form that is released continuously inside the body.

14. The method according to claim 13, wherein the angiotensin-(1-9) peptide is administered with through a continuous release pump.

15. The method according to claim 4, wherein the angiotensin-(1-9) peptide is administered with through a continuous release pump.

16. The method according to claim 5, wherein the angiotensin-(1-9) peptide is administered with through a continuous release pump.

17. The method according to claim 13, wherein said continuous release is carried out via intravenous, intramuscular, intradermal, subcutaneous, or intraperitoneal route.

18. The method according to claim 14, wherein said continuous release is carried out via intravenous, intramuscular, intradermal, subcutaneous, or intraperitoneal route.

19. The method according to claim 5, wherein said continuous release is carried out via intravenous, intramuscular, intradermal, subcutaneous, or intraperitoneal route.

20. The method according to claim 2, wherein the angiotensin-(1-9) peptide is in oral or rectal pharmaceutical form.

21. The method according to claim 1, wherein said angiotensin-(1-9) peptide is administered with an adjuvant.

22. The method according to claim 1, wherein said angiotensin-(1-9) peptide is administered with a preservative.

23. The method according to claim 2, wherein said angiotensin-(1-9) peptide is administered with an adjuvant.

24. The method according to claim 2, wherein said angiotensin-(1-9) peptide is administered with a preservative.

* * * * *

SEQUENCE LISTING

```
<160> NUMBER OF SEQ ID NOS: 7

<210> SEQ ID NO 1
<211> LENGTH: 14
<212> TYPE: PRT
<213> ORGANISM: Artificial Sequence
<220> FEATURE:
<223> OTHER INFORMATION: Synthetic peptide: Angiotensinogen

<400> SEQUENCE: 1

Asp Arg Val Tyr Ile His Pro Phe His Leu Leu Val Tyr Ser
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic peptide: Angiotensin 1

<400> SEQUENCE: 2

Asp Arg Val Tyr Ile His Pro Phe His Leu
1               5                   10

<210> SEQ ID NO 3
<211> LENGTH: 8
<212> TYPE: PRT
<213> ORGANISM: Artificial Sequence
<220> FEATURE:
<223> OTHER INFORMATION: Synthetic peptide: Angiotensin II

<400> SEQUENCE: 3

Asp Arg Val Tyr Ile His Pro Phe
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide: Angiotensin III

<400> SEQUENCE: 4

Arg Val Tyr Ile His Pro Phe
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide: Angiotensin-IV

<400> SEQUENCE: 5

Val Tyr Ile His Pro Phe
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide: Angiotensin-(1-9)

<400> SEQUENCE: 6

Asp Arg Val Tyr Ile His Pro Phe His
1               5
```

```
<210> SEQ ID NO 7
<211> LENGTH: 7
<212> TYPE: PRT
<213> ORGANISM: Artificial Sequence
<220> FEATURE:
<223> OTHER INFORMATION: Synthetic peptide: Angiotensin-(1-7)

<400> SEQUENCE: 7

Asp Arg Val Tyr Ile His Pro
1               5
```